(12) United States Patent
Konstantino et al.

(10) Patent No.: US 8,080,026 B2
(45) Date of Patent: Dec. 20, 2011

(54) APPARATUS AND METHODS FOR TREATING HARDENED VASCULAR LESIONS

(75) Inventors: Eitan Konstantino, Orinda, CA (US); Tanhum Feld, Moshav Merhavya (IL); Nimrod Tzori, Sunnyvale, CA (US)

(73) Assignee: AngioScore, Inc., Fremont, CA (US)

( * ) Notice: Subject to any disclaimer, the term of this patent is extended or adjusted under 35 U.S.C. 154(b) by 1967 days.

(21) Appl. No.: 10/917,917

(22) Filed: Aug. 13, 2004

(65) Prior Publication Data

US 2005/0021071 A1  Jan. 27, 2005

Related U.S. Application Data

(63) Continuation-in-part of application No. 10/810,330, filed on Mar. 25, 2004, now Pat. No. 7,955,350, which is a continuation-in-part of application No. 10/631,499, filed on Jul. 30, 2003, now Pat. No. 7,686,824.

(60) Provisional application No. 60/442,161, filed on Jan. 21, 2003.

(51) Int. Cl.
*A61B 17/22* (2006.01)
(52) U.S. Cl. ........................ 606/159; 623/1.11
(58) Field of Classification Search .............. 606/159, 606/194; 604/22, 500; 623/1.11
See application file for complete search history.

(56) References Cited

U.S. PATENT DOCUMENTS

| | | | |
|---|---|---|---|
| 4,604,762 A | 8/1986 | Robinson | |
| 4,649,922 A | 3/1987 | Wiktor | |
| 4,838,853 A | 6/1989 | Parisi | |
| 4,887,613 A | 12/1989 | Farr et al. | |
| 4,895,166 A | 1/1990 | Farr et al. | |
| 4,921,484 A | 5/1990 | Hillstead | |
| 4,942,788 A | 7/1990 | Farr et al. | |
| 4,950,277 A | 8/1990 | Farr | |
| 4,966,604 A | 10/1990 | Reiss | |
| 4,969,458 A | 11/1990 | Wiktor | |
| 4,986,807 A | 1/1991 | Farr | |
| 4,998,539 A | 3/1991 | Delsanti | |
| 5,003,918 A | 4/1991 | Olson et al. | |
| 5,019,088 A | 5/1991 | Farr | |

(Continued)

FOREIGN PATENT DOCUMENTS

EP  1169970 A1  1/2002

(Continued)

OTHER PUBLICATIONS

Office Action of Japanese Patent Application No. 2007-505113, mailed on Jul. 9, 2010, 8 pages total (English Translation Included).

(Continued)

*Primary Examiner* — Victor Nguyen
(74) *Attorney, Agent, or Firm* — Wilson Sonsini Goodrich & Rosati

(57) ABSTRACT

An angioplasty catheter comprises a catheter body having a balloon or other radially expandable shell at its distal end. A non-axial external structure is carried over the shell and scores a stenosed region in a blood vessel when the balloon is inflated therein. The catheter has an attachment structure disposed between the catheter body and the balloon to accommodate foreshortening and rotation of the external structure as the balloon is expanded. The external structure may be part of a helical cage structure which floats over the balloon.

49 Claims, 15 Drawing Sheets

U.S. PATENT DOCUMENTS

| | | | |
|---|---|---|---|
| 5,019,089 A | 5/1991 | Farr | |
| 5,026,384 A | 6/1991 | Farr et al. | |
| 5,062,648 A | 11/1991 | Gomringer | |
| 5,098,440 A | 3/1992 | Hillstead | |
| 5,100,423 A | 3/1992 | Fearnot | |
| 5,101,682 A | 4/1992 | Radisch, Jr. et al. | |
| 5,102,402 A | 4/1992 | Dror et al. | |
| 5,108,416 A | 4/1992 | Ryan et al. | |
| 5,112,345 A | 5/1992 | Farr | |
| 5,116,318 A | 5/1992 | Hillstead | |
| 5,120,322 A | 6/1992 | Davis et al. | |
| 5,133,732 A | 7/1992 | Wiktor | |
| 5,176,693 A | 1/1993 | Pannek, Jr. | |
| 5,192,291 A | 3/1993 | Pannek, Jr. | |
| 5,196,024 A | 3/1993 | Barath | |
| 5,209,727 A | 5/1993 | Radisch, Jr. et al. | |
| 5,221,261 A | 6/1993 | Termin et al. | |
| 5,224,945 A | 7/1993 | Pannek, Jr. | |
| 5,224,949 A | 7/1993 | Gomringer et al. | |
| 5,226,887 A | 7/1993 | Farr et al. | |
| 5,243,997 A | 9/1993 | Uflacker et al. | |
| 5,295,493 A | 3/1994 | Radisch, Jr. | |
| 5,295,959 A | 3/1994 | Gurbel et al. | |
| 5,304,121 A | 4/1994 | Sahatjian | |
| 5,306,250 A | 4/1994 | March et al. | |
| 5,308,354 A | 5/1994 | Zacca et al. | |
| 5,318,576 A | 6/1994 | Weiss et al. | |
| 5,320,634 A | 6/1994 | Vigil et al. | |
| 5,336,234 A | 8/1994 | Vigil et al. | |
| 5,344,401 A | 9/1994 | Radisch et al. | |
| 5,350,101 A | 9/1994 | Godlewski | |
| 5,376,077 A | 12/1994 | Gomringer | |
| 5,423,745 A | 6/1995 | Todd et al. | |
| 5,443,078 A | 8/1995 | Uflacker | |
| 5,443,496 A | 8/1995 | Schwartz et al. | |
| 5,456,667 A | 10/1995 | Ham et al. | |
| 5,458,568 A | 10/1995 | Racchini et al. | |
| 5,470,314 A | 11/1995 | Walinsky | |
| 5,524,635 A | 6/1996 | Uflacker et al. | |
| 5,545,132 A | 8/1996 | Fagan et al. | |
| 5,556,405 A | 9/1996 | Lary | |
| 5,556,408 A | 9/1996 | Farhat | |
| 5,569,195 A * | 10/1996 | Saab | 604/103.13 |
| 5,571,086 A | 11/1996 | Kaplan et al. | |
| 5,616,149 A | 4/1997 | Barath | |
| 5,624,433 A | 4/1997 | Radisch, Jr. | |
| 5,649,941 A | 7/1997 | Lary | |
| 5,681,281 A | 10/1997 | Vigil et al. | |
| 5,697,944 A | 12/1997 | Lary | |
| 5,697,971 A | 12/1997 | Fischell et al. | |
| 5,707,385 A | 1/1998 | Williams | |
| 5,713,863 A | 2/1998 | Vigil et al. | |
| 5,713,913 A | 2/1998 | Lary et al. | |
| 5,735,816 A | 4/1998 | Lieber et al. | |
| 5,742,019 A | 4/1998 | Radisch, Jr. | |
| 5,746,716 A | 5/1998 | Vigil et al. | |
| 5,746,968 A | 5/1998 | Radisch, Jr. | |
| 5,755,778 A | 5/1998 | Kleshinski | |
| 5,779,698 A | 7/1998 | Clayman et al. | |
| 5,792,415 A | 8/1998 | Hijlkema | |
| 5,797,935 A * | 8/1998 | Barath | 606/159 |
| 5,800,450 A | 9/1998 | Lary et al. | |
| 5,868,719 A | 2/1999 | Tsukernik | |
| 5,868,779 A * | 2/1999 | Ruiz | 606/194 |
| 5,873,852 A | 2/1999 | Vigil et al. | |
| 5,891,090 A | 4/1999 | Thornton | |
| 5,902,475 A | 5/1999 | Trozera et al. | |
| 5,916,166 A | 6/1999 | Reiss et al. | |
| 5,994,667 A | 11/1999 | Merdan et al. | |
| 6,036,689 A * | 3/2000 | Tu et al. | 606/41 |
| 6,053,913 A | 4/2000 | Tu et al. | |
| 6,071,285 A | 6/2000 | Lashinski et al. | |
| 6,071,286 A | 6/2000 | Mawad | |
| 6,077,298 A | 6/2000 | Tu et al. | |
| RE36,764 E | 7/2000 | Zacca et al. | |
| 6,102,904 A | 8/2000 | Vigil et al. | |
| 6,106,548 A | 8/2000 | Roubin et al. | |
| 6,117,104 A | 9/2000 | Fitz | |
| 6,117,153 A | 9/2000 | Lary et al. | |
| 6,123,718 A | 9/2000 | Tu et al. | |
| 6,129,706 A | 10/2000 | Janacek | |
| 6,136,011 A | 10/2000 | Stambaugh | |
| 6,152,944 A | 11/2000 | Holman et al. | |
| 6,156,254 A | 12/2000 | Andrews et al. | |
| 6,165,187 A | 12/2000 | Reger | |
| 6,190,356 B1 | 2/2001 | Bersin | |
| 6,210,392 B1 | 4/2001 | Vigil et al. | |
| 6,245,040 B1 | 6/2001 | Inderbitzen et al. | |
| 6,258,108 B1 | 7/2001 | Lary | |
| 6,296,651 B1 | 10/2001 | Lary et al. | |
| 6,306,151 B1 | 10/2001 | Lary | |
| 6,312,459 B1 | 11/2001 | Huang et al. | |
| 6,325,779 B1 | 12/2001 | Zedler | |
| 6,332,880 B1 | 12/2001 | Yang et al. | |
| 6,355,013 B1 | 3/2002 | van Muiden | |
| 6,355,059 B1 | 3/2002 | Richter et al. | |
| 6,364,856 B1 | 4/2002 | Ding et al. | |
| 6,371,961 B1 | 4/2002 | Osborne et al. | |
| 6,394,995 B1 | 5/2002 | Solar et al. | |
| 6,416,494 B1 | 7/2002 | Wilkins | |
| 6,425,882 B1 | 7/2002 | Vigil | |
| 6,440,158 B1 | 8/2002 | Saab | |
| 6,447,501 B1 | 9/2002 | Solar et al. | |
| 6,450,988 B1 | 9/2002 | Bradshaw | |
| 6,450,989 B2 | 9/2002 | Dubrul et al. | |
| 6,454,775 B1 | 9/2002 | Demarais et al. | |
| 6,471,979 B2 | 10/2002 | New et al. | |
| 6,475,233 B2 | 11/2002 | Trozera | |
| 6,475,234 B1 | 11/2002 | Richter et al. | |
| 6,517,765 B1 | 2/2003 | Kelley | |
| 6,562,062 B2 | 5/2003 | Jenusaitis et al. | |
| 6,565,528 B1 | 5/2003 | Mueller | |
| 6,569,180 B1 | 5/2003 | Sirhan et al. | |
| 6,592,548 B2 | 7/2003 | Jayaraman | |
| 6,605,107 B1 | 8/2003 | Klein | |
| 6,648,912 B2 | 11/2003 | Trout, III et al. | |
| 6,939,320 B2 | 9/2005 | Lennox | |
| 7,011,654 B2 | 3/2006 | Dubrul et al. | |
| 7,060,051 B2 | 6/2006 | Palasis | |
| 7,494,497 B2 | 2/2009 | Weber | |
| 7,686,824 B2 | 3/2010 | Konstantino et al. | |
| 7,955,350 B2 | 6/2011 | Konstantino et al. | |
| 2002/0010487 A1 | 1/2002 | Demarais et al. | |
| 2002/0010489 A1 | 1/2002 | Grayzel et al. | |
| 2002/0029015 A1 * | 3/2002 | Camenzind et al. | 604/97.02 |
| 2002/0038144 A1 | 3/2002 | Trout, III et al. | |
| 2002/0065548 A1 | 5/2002 | Birdsall et al. | |
| 2002/0091438 A1 | 7/2002 | Trozera | |
| 2002/0165599 A1 | 11/2002 | Nasralla | |
| 2002/0193873 A1 | 12/2002 | Brucker et al. | |
| 2003/0018376 A1 | 1/2003 | Solar et al. | |
| 2003/0032973 A1 | 2/2003 | Jenusaitis et al. | |
| 2003/0065381 A1 | 4/2003 | Solar et al. | |
| 2003/0074046 A1 | 4/2003 | Richter | |
| 2003/0097169 A1 | 5/2003 | Brucker et al. | |
| 2003/0105509 A1 | 6/2003 | Jang et al. | |
| 2003/0144683 A1 | 7/2003 | Sirhan et al. | |
| 2003/0149468 A1 | 8/2003 | Wallsten | |
| 2003/0153870 A1 | 8/2003 | Meyer et al. | |
| 2003/0171799 A1 | 9/2003 | Lee et al. | |
| 2003/0195609 A1 | 10/2003 | Berenstein et al. | |
| 2003/0199970 A1 | 10/2003 | Shanley | |
| 2003/0199988 A1 | 10/2003 | Devonec et al. | |
| 2003/0208255 A1 | 11/2003 | O'Shaughnessy et al. | |
| 2004/0111108 A1 | 6/2004 | Farnan | |
| 2004/0127475 A1 | 7/2004 | New et al. | |
| 2005/0010278 A1 | 1/2005 | Vardi et al. | |
| 2005/0021070 A1 | 1/2005 | Feld et al. | |
| 2005/0083768 A1 | 4/2005 | Hara | |
| 2005/0119723 A1 | 6/2005 | Peacock, III | |
| 2005/0288629 A1 | 12/2005 | Kunis | |
| 2006/0004323 A1 | 1/2006 | Chang et al. | |
| 2006/0020243 A1 | 1/2006 | Speck et al. | |
| 2006/0112536 A1 | 6/2006 | Herweck et al. | |
| 2006/0129093 A1 | 6/2006 | Jackson | |
| 2006/0149308 A1 | 7/2006 | Melsheimer et al. | |

| | | | |
|---|---|---|---|
| 2006/0184191 A1 | 8/2006 | O'Brien | |
| 2006/0247674 A1 | 11/2006 | Roman | |
| 2006/0259062 A1 | 11/2006 | Konstantino | |

FOREIGN PATENT DOCUMENTS

| | | |
|---|---|---|
| JP | 2002-126086 A | 5/2002 |
| WO | WO 91/02494 A1 | 3/1991 |
| WO | WO 93/01753 A2 | 2/1993 |
| WO | WO 93/01753 A3 | 4/1993 |
| WO | WO 94/10919 A1 | 5/1994 |
| WO | WO 94/23787 A1 | 10/1994 |
| WO | WO 94/24946 | 11/1994 |
| WO | WO 95/03083 A1 | 2/1995 |
| WO | WO 98/45506 A1 | 10/1998 |
| WO | WO 02/083011 | 10/2002 |
| WO | WO 03/026536 A1 | 4/2003 |
| WO | WO 03/039628 A2 | 5/2003 |
| WO | WO 03/041760 A2 | 5/2003 |
| WO | WO 03/039628 A3 | 10/2003 |
| WO | WO 03/041760 A3 | 4/2004 |
| WO | WO 2004/028610 A2 | 4/2004 |
| WO | WO 2004/028610 A3 | 6/2004 |
| WO | WO 2004/060460 A2 | 7/2004 |
| WO | WO 2004/066852 A2 | 8/2004 |
| WO | WO 2004/060460 A3 | 11/2004 |
| WO | WO 2004/066852 A3 | 1/2005 |
| WO | WO 2005/025458 A1 | 3/2005 |

OTHER PUBLICATIONS

European search report and search opinion dated May 4, 2010 for EP 06770116.9.

European search report and search opinion dated Dec. 28, 2009 for EP 05792875.6.

International search report and written opinion dated May 23, 2006 for PCT/US2005/009571.

International search report and written opinion dated Jul. 26, 2007 for PCT/US2005/028809.

International search report and written opinion dated Nov. 4, 2004 for PCT/US2004/000177.

* cited by examiner

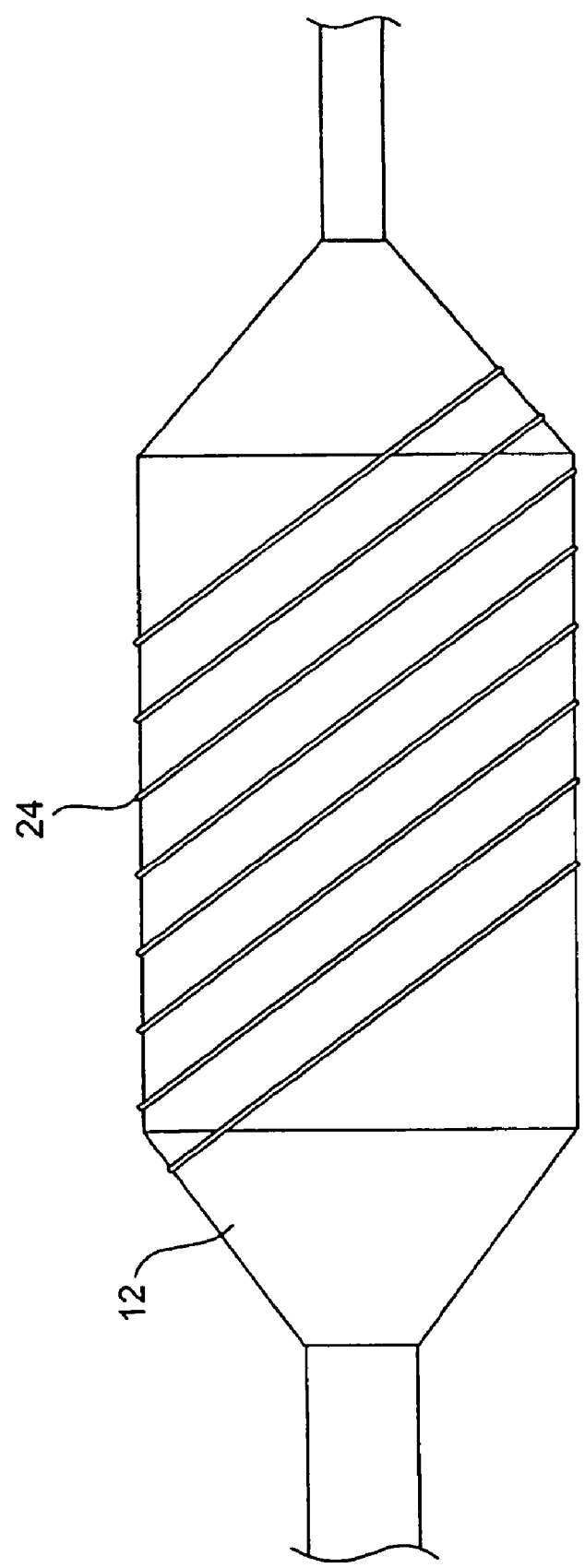

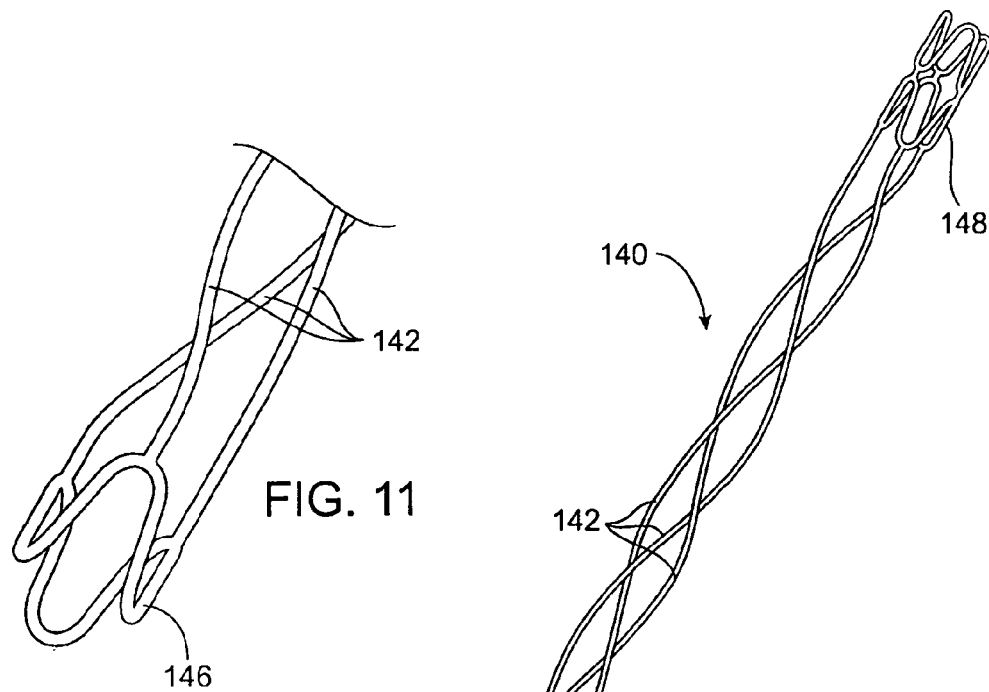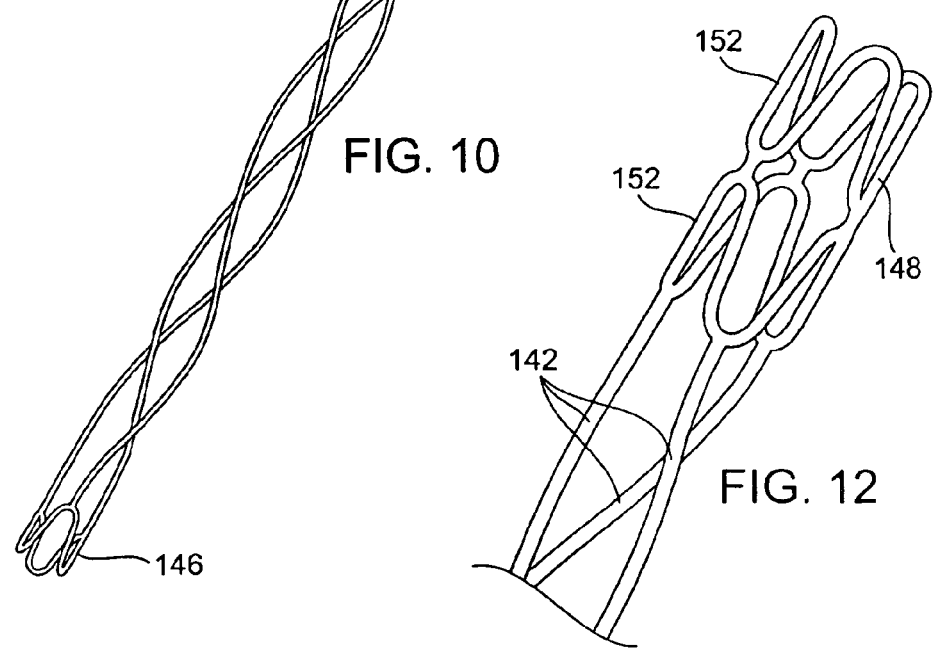

APPARATUS AND METHODS FOR TREATING HARDENED VASCULAR LESIONS

CROSS-REFERENCES TO RELATED APPLICATIONS

This application is a continuation-in-part of commonly assigned, co-pending U.S. application Ser. No. 10/810,330, filed on Mar. 25, 2004, which is a continuation in part of U.S. application Ser. No. 10/631,499, filed on Jul. 30, 2003, which claims the benefit under 35 USC §119(e) of U.S. Provisional Application No. 60/442,161, filed on Jan. 21, 2003, the full disclosures of which are incorporated herein by reference.

BACKGROUND OF THE INVENTION

1. Field of the Invention

The present invention relates to the field of medical devices, more specifically medical to devices intended to treat stenoses in the vascular system.

Balloon dilatation (angioplasty) is a common medical procedure mainly directed at revascularization of stenotic vessels by inserting a catheter having a dilatation balloon through the vascular system. The balloon is inflated inside a stenosed region in a blood vessel in order to apply radial pressure to the inner wall of the vessel and widen the stenosed region to enable better blood flow.

In many cases, the balloon dilatation procedure is immediately followed by a stenting procedure where a stent is placed to maintain vessel patency following the angioplasty. Failure of the angioplasty balloon to properly widen the stenotic vessel, however, may result in improper positioning of the stent in the blood vessel. If a drug-eluting stent is used, its effectiveness may be impaired by such improper positioning and the resulting restenosis rate may be higher. This is a result of several factors, including the presence of gaps between the stent and the vessel wall, calcified areas that were not treated properly by the balloon, and others.

Conventional balloon angioplasty suffers from a number of other shortcomings as well. In some cases the balloon dilatation procedure causes damage to the blood vessel due to aggressive balloon inflation that may stretch the diseased vessel beyond its elastic limits. Such over inflation may damage the vessel wall and lead to restenosis of the section that was stretched by the balloon. In other cases, slippage of the balloon during the dilatation procedure may occur. This may result in injury to the vessel wall surrounding the treated lesion. One procedure in which slippage is likely to happen is during treatment of in-stent restenosis, which at present is difficult to treat by angioplasty balloons. Fibrotic lesions are also hard to treat with conventional balloons, and elastic recoil is usually observed after treatment of these lesions. Many long lesions have fibrotic sections that are difficult to treat using angioplasty balloons.

An additional problem associated with balloon angioplasty treatment has been the "watermelon seed effect." Angioplasty is carried out at very high pressures, typically up to twenty atmospheres or higher, and the radially outward pressure of the balloon can cause axial displacement of the balloon in a manner similar to squeezing a watermelon seed with the fingers. Such axial displacement, of course, reduces the effectiveness of balloon dilatation. Another problem with conventional angioplasty balloon design has been deflation of the balloon. Even after the inflation medium is removed from a balloon, the deflated configuration will have a width greater than the original folded configuration which was introduced to the vasculature. Such an increase in profile can make removal of the balloon difficult.

Atherectomy/Thrombectomy devices intended to remove plaque/thrombus material may also include a structure that expands in a lesion while the plaque/thrombus removal mechanism is within this structure. The removed material is either being stacked in the catheter or sucked out thru the catheter. When the procedure is done, the expandable structure is collapsed and the catheter removed. Foreign object removal devices usually include a basket structure that needs to be expanded to collect the object and then collapse for retrieval. Distal protection devices usually include a basket structure that support a mesh that needs to be expanded distal to the treated lesion to collect the loose objects and then collapse for retrieval.

These devices usually include an elastic metallic material that needs to be expanded in the vascular system to fulfill its task and afterwards collapse to a small diameter to facilitate retrieval. The transition between the collapsed (closed) configuration to the expanded (open) configuration can be done in two ways: the structure can be at a normally closed (collapsed) configuration in which force is applied to cause the structure to expand. In this case, the elastic recoil of the structure will cause it to collapse back to closed configuration when the expanding force ceases. The structure may also be at a normally open (expanded) configuration in which a constraining element is forced over it to hold it dawn for the collapsed configuration (for example a constraining tube). When this constraining element is removed the structure is free to expand to the expanded (open) configuration. The structure material may also be non elastic. In this case, the structure will need to be forced to transit between both collapsed and expanded configuration.

One problem associated with conventional angioplasty expansion systems is that the transition between the collapsed and expanded configurations involves significant rotational and axial reaction forces. These reaction forces are applied by the structure on the catheter as a result of the force applied by the catheter to expand or close the structure. Axial reaction forces are created due the foreshortening of the structure during expansion. Rotational reaction forces (torques) are created when a non longitudinal element is forced to expand/collapse. Since the catheters are usually less stiff the structure, these reaction forces may cause that the structure will not expand or collapse properly, or cause undesired deformation to the catheter itself.

To overcome at least some of these problems these problems, U.S. Pat. No. 5,320,634 describes the addition of cutting blades to the balloon. The blades can cut the lesions as the balloon is inflated. U.S. Pat. No. 5,616,149 describes a similar method of attaching sharp cutting edges to the balloon. U.S. Patent Publication 2003/0032973 describes a stent-like structure having non-axial grips for securing an angioplasty balloon during inflation. U.S. Pat. No. 6,129,706 describes a balloon catheter having bumps on its outer surface. U.S. Pat. No. 6,394,995 describes a method of reducing the balloon profile to allow crossing of tight lesions. U.S. Patent Publication 2003/0153870 describes a balloon angioplasty catheter having a flexible elongate elements that create longitudinal channels in a lesion or stenosis.

While the use of angioplasty balloons having cutting blades has proved to be a significant advantage under many circumstances, the present cutting balloon designs and methods for their use continue to suffer from shortcomings. Most commercial cutting balloon designs, including those available from INTERVENTIONAL TECHNOLOGIES, INC., of San Diego, Calif., now owned by BOSTON SCIENTIFIC, of Natick, Mass., have relatively long, axially aligned blades carried on the outer surface of an angioplasty balloon. Typically, the blades are carried on a relatively rigid base directly attached to the outer balloon surface. The addition of such rigid, elongated blade structures makes the balloon itself quite stiff and limits the ability to introduce the balloon through torturous regions of the vasculature, particularly the smaller vessels within the coronary vasculature. Moreover, the cutting balloons can be difficult to deflate and collapse, making removal of the balloons from the vasculature more difficult than with corresponding angioplasty balloons which do not include cutting blades. Additionally, the axially oriented cuts imparted by such conventional cutting balloons do not always provide the improved dilatation and treatment of fibrotic lesions which would be desired.

For these reasons, it would be desirable to provide improved cutting balloon designs and methods for their use. In particular, it would be desirable to provide cutting balloons which are highly flexible over the length of the balloon structure, which readily permit deflation and facilitate removal from the vasculature, and which are effective in treating all forms of vascular stenoses, including but not limited to treatment of highly calcified plaque regions of diseased arteries, treatment of small vessels and/or vessel bifurcations that will not be stented, treatment of ostial lesions, and treatment of in-stent restenosis (ISR). Moreover, it would be desirable if such balloon structures and methods for their use could provide for improved anchoring of the balloon during dilatation of the stenosed region.

It would further be desirable to minimize the reaction forces applied by the external structure to the catheter, and at the same time be able to control the expansion of the expandable structure. It would also be desirable to adjust the compliance of the system in a predictable way without changing the materials or geometry of the expandable structure. At least some of these objectives will be met with the inventions described hereinafter.

2. Description of the Background Art

The following U.S. patents and printed publication relate to cutting balloons and balloon structures: U.S. Pat. Nos. 6,450,988; 6,425,882; 6,394,995; 6,355,013; 6,245,040; 6,210,392; 6,190,356; 6,129,706; 6,123,718; 5,891,090; 5,797,935; 5,779,698; 5,735,816; 5,624,433; 5,616,149; 5,545,132; 5,470,314; 5,320,634; 5,221,261; 5,196,024; and Published U.S. Pat. App. 2003/0032973. Other U.S. patents of interest include U.S. Pat. Nos. 6,454,775; 5,100,423, 4,998,539; 4,969,458; and 4,921,984.

SUMMARY OF THE INVENTION

The present invention provides improved apparatus and methods for the dilatation of stenosed regions in the vasculature. The stenosed regions will often include areas of fibrotic, calcified, or otherwise hardened plaque or other stenotic material of the type which can be difficult to dilatate using conventional angioplasty balloons. The methods and apparatus will often find their greatest use in treatment of the arterial vasculature, including but not limited to the coronary arterial vasculature, but may also find use in treatment of the venous and/or peripheral vasculature, treatment of small vessels and/or vessel bifurcations that will not be stented, treatment of ostial lesions, and treatment of ISR.

In a first aspect of the present invention, a scoring catheter comprises a catheter body having a proximal end and a distal end, a radially expandable shell (typically an angioplasty balloon) near the distal end of the catheter body, and a non-axial scoring structure carried over the shell. By "non-axial scoring structure," it is meant that the structure will be able to score or cut stenotic material within a treated blood vessel along lines which are generally in a non-axial direction. For example, the scoring lines may be helical, serpentine, zig-zag, or may combine some axial components together with such non-axial components. Usually, the non-axial scoring pattern which is imparted will include scoring segments which, when taken in total, circumscribe at least a majority of and usually the entire inside wall of the blood vessel up to one time, preferably more than one time, usually more than two times, often at least three times, more often at least four, five, six, or more times. It is believed that the resulting scoring patterns which circumscribes the inner wall of the vessel will provide improved results during subsequent balloon dilatation.

Usually the scoring structure will comprise at least one continuous, i.e., non-broken, scoring element having a length of at least 0.5 cm, more usually at least 1 cm, often at least 2 cm, usually at least 3 cm, and sometimes at least 4 cm or more. Alternatively, the scoring structure may comprise a plurality of much smaller segments which may be arranged in a helical or other pattern over the balloon, typically having a length in the range from 0.1 cm to 2 cm, often being 0.5 cm or less, sometimes being 0.3 cm or less.

In order to promote scoring of the blood vessel wall when the underlying expandable shell is expanded, the scoring structure will usually have a vessel contact area which is 20% or less of the area of the expandable shell, usually being below 10%, and often being in the range from 1% to 5% of the area of the expandable shell. The use of a shell having such a relatively small contact area increases the amount of force applied to the vascular wall through the structure by expansion of the underlying expandable shell. The scoring structure can have a variety of particular configurations, often being in the form of a wire or slotted tube having a circular, square, or other cross-sectional geometry. Preferably, the components of the scoring structure will comprise a scoring edge, either in the form of a honed blade, a square shoulder, or the like. A presently preferred scoring edge is electropolished and relatively small.

In a preferred embodiment, the scoring structure may be formed as a separate expandable cage which is positioned over the expandable shell of the catheter. The cage will usually have a collar or other attachment structure at each end for placement on the catheter body on either side of the expandable shell. A collar may be a simple tube, and other attachment structures will usually be crimpable or otherwise mechanically attachable to the catheter body, such as a serpentine or other ring structure. The attachment structures on the cage may be attached at both ends to the catheter body, but will more usually be attached at only a single end with the other end being allowed to float freely. Such freedom allows the scoring structure to shorten as the structure is expanded on the expandable shell. In certain embodiments, both ends of the scoring structure will be fixed to the catheter body, but at least one of the attachment structures will have a spring or other compliant attachment component which provides an axial extension as the center of the scoring structure foreshortens.

In many cases, since the scoring elements are non-axial, there are torques induced during the expansion of the balloon and the shortening of the scoring structure. These torques may be high, and if one end of the scoring structure is constrained from rotation, the scoring element will not expand properly. The final expanded configuration of the scoring element is achieved via shortening and rotation.

In a preferred embodiment, both sides of the scoring element are fixed to the catheter, but at least one side will have a compliant structure which will provide axial tension and at the same time will allow the scoring element to rotate to its final configuration.

In some cases both ends of the scoring element are fixed and the shortening is achieved by deformation of the wire. For example, the wire can have a secondary structure which permits elongation (e.g., it may be a coiled filament) or can be formed from a material which permits elongation, e.g., nitinol. The scoring element can be attached in both ends, in a way that will allow rotation. In the case were the torques are low (depending on the design of the scoring element) there is no need for rotation and the torque can be absorbed either be the scoring element of by the catheter.

In all cases, the scoring structure is preferably composed of an elastic material, more preferably a super elastic material, such as nitinol. The scoring structure is thus elastically expanded over the expandable shell, typically an inflatable balloon similar to a conventional angioplasty balloon. Upon deflation, the scoring structure will elastically close to its original non-expanded configuration, thus helping to close and contain the balloon or other expandable shell.

In some cases the scoring element will be a combination of more than one material. In one case the scoring element can be made from nitinol and parts of it can be made from stainless steel. In other cases the scoring element can be made of stainless steel or nitinol and part of it can be made from polymer to allow high deformations.

In other preferred embodiments, the assembly of the shell and the scoring structure will be sufficiently flexible to permit passage through tortuous regions of the vasculature, e.g., being capable of bending at radius of 10 mm or below when advanced through 45°, 90° or higher bends in the coronary vasculature. Usually, the scoring structure will comprise one or more scoring elements, wherein less than 70% of the cumulative length of the scoring element is aligned axially on the shell when expanded, preferably being less than 50% of the cumulative length, and more preferably being less than 25% of the cumulative length. In other instances, the scoring structure may comprise one or more scoring elements, wherein the cumulative length of the scoring element includes a non-axial component of at least 10 mm, preferably at least 12 mm, and more preferably 36 mm. Preferably, at least some of the scoring elements will have scoring edges which are oriented radially outwardly along at least a major portion of their lengths at all times during inflation and deflation and while inflated. By "radially outward," it is meant that a sharp edge or shoulder of the element will be oriented to score or cut into the stenotic material or the interior wall of the treated vessel, particularly as the shell is being inflated.

The scoring elements will usually, but not necessarily, have a scoring edge formed over at least a portion of their lengths. A "scoring edge" may comprise a sharpened or honed region, like a knife blade, or a square shoulder as in scissors or other shearing elements. Alternatively, the scoring elements may be free from defined scoring edges, e.g., having circular or the other non-cutting profiles. Such circular scoring elements will concentrate the radially outward force of the balloon to cause scoring or other disruption of the plaque or other stenotic material being treated.

In a second aspect of the present invention, the scoring catheter comprises a catheter body and a radially expandable shell, generally as set forth above. The scoring structure will be composed of elements which circumscribe the radially expandable shell. By "circumscribing the radially expandable shell," it is meant that at least some scoring elements of the scoring structure will form a continuous peripheral path about the exterior of the expandable shell during expansion. An example of such a fully circumscribing structure is a helical structure which completes up to one 360° path about the balloon before, during and after expansion, usually completing two complete revolutions, and frequently completing three, four, or more complete revolutions. Exemplary helical structures may include two, three, four, or more separate elements, each of which is helically arranged around the radially expandable shell.

In a third aspect of the present invention, a scoring catheter comprises a catheter body and a radially expandable shell, generally as set forth above. An elongated scoring structure is carried over the shell, and the assembly of the shell and the scoring structure will be highly flexible to facilitate introduction over a guide wire, preferably being sufficiently flexible when unexpanded so that it can be bent at an angle of at least 90°, preferably 180°, at a radius of 1 cm without kinking or otherwise being damaged. Such flexibility can be determined, for example, by providing a solid cylinder having a radius of 1 cm and conforming the assembly of the scoring structure and expandable shell over the cylinder. Alternatively, the assembly can be advanced over a guide wire or similar element having a 180° one centimeter radius bend. In either case, if assembly bends without kinking or other damage, it meets the requirement described above. Other specific features in this further embodiment of the catheters of the present invention are as described above in connection with the prior embodiments.

In a fourth aspect of the present invention, a plaque scoring catheter comprises a catheter body and a radially expandable balloon, generally as set forth above. A plurality of scoring elements are distributed over the balloon, typically being attached directly to an outer surface of the balloon. The scoring elements will be relatively short, typically having lengths below about 25% of the balloon length, preferably having lengths in the range from 2% to 10% of the balloon length. The relatively short, segmented scoring elements will permit highly flexible assemblies of balloon and scoring elements, generally meeting the flexibility requirement set forth above. The scoring elements may be arranged randomly over the balloon but will more usually be distributed uniformly over the balloon. In specific embodiments, the scoring elements may be arranged in helical, serpentine, or other regular patterns which circumscribe the balloon. As the balloon expands, such short segments will generally move apart from each other, but will still impart the desired scoring patterns into the vascular wall as the balloon is inflated.

In a fifth embodiment, the scoring catheter according to the present invention comprises a catheter body and a radially expandable balloon generally as set forth above. The balloon has a plurality of lobes extending between ends of the balloons, and at least one scoring element will be formed on at least one of the lobes in a manner arranged to score stenotic material as the balloon is expanded. The lobe will usually be in a helical pattern, and typically two, three, or more lobes will be provided. In the case of helical lobes, the scoring element(s) will usually be disposed along a helical peak defined by the helical lobe when the balloon is inflated. Such helical scoring elements will be arranged to accommodate balloon inflation, typically being stretchable, segmented, or the like.

In still another aspect of the apparatus of the present invention, an expandable scoring cage is adapted to be carried over a balloon of a balloon catheter. The scoring cage comprises an assembly of one or more elongate elastic scoring elements arranged in a non-axial pattern. As defined above, the non-axial pattern may comprise both axial and non-axial segments. The assembly is normally in a radially collapsed configuration and is expandable over a balloon to a radially expanded configuration. After the balloon is deflated, the assembly returns to a radially collapsed configuration, preferably being assisted by the elastic nature of the scoring cage. Advantageously, the scoring cage will enhance uniform expansion of the underlying balloon or other expandable shell and will inhibit "dog boning" where an angioplasty balloon tends to over inflate at each end, increasing the risk of vessel dissection. The scoring elements will be adapted to score hardened stenotic material, such as plaque or fibrotic material, when expanded by the balloon in a blood vessel lumen. The scoring cage may be adapted to mount over the balloon with either or both ends affixed to the balloon, generally as described above in connection with prior embodiments. Preferred geometries for the scoring elements include those which circumscribe the balloon, those which are arranged helically over the balloon, those which are arranged in a serpentine pattern over balloon and the like.

In yet another aspect of the present invention, a method for dilatating a stenosed region in a blood vessel comprises radially expanding a shell which carries a scoring structure. The scoring structure scores and dilates the stenosed region and includes one or more non-axial scoring elements arranged to impart a circumscribing score pattern about the inner wall of the blood vessel as the shell is expanded. The stenosed region is typically characterized by the presence of calcified plaque, fibrotic plaque, or other hardened stenotic material which is preferably scored prior to dilatation. Preferably, the scoring structure will not be moved in axial direction while engaged against the stenosed region, and the scoring structure may optionally be free from axially scoring elements.

In still another aspect of the present invention, an angioplasty catheter comprises a catheter body and a radially expandable shell near the distal end of the catheter body. An external structure, such as a scoring structure or cutting structure, is carried over but unattached to the shell. The catheter further comprises an attachment structure having a proximal end and a distal end attached to the scoring structure, wherein the attachment structure is sufficiently sized and compliant to accommodate reaction forces or geometrical changes produced by the scoring structure as it is expanded by the shell. Generally, at least a portion of said scoring structure is arranged helically over the shell. However, the scoring structure may comprise numerous different configurations as described above.

In one aspect of the present invention, the proximal end of the attachment structure is fixed to the catheter body and the distal end of the attachment structure is secured to the proximal end of the scoring structure. In all cases, the attachment structure is capable axially and rotationally extending to accommodate foreshortening of the scoring structure as the shell is expanded.

In a preferred embodiment, the attachment structure comprises a compliance tube having an outer diameter and an inner diameter that extends over the catheter body. The inner diameter of the compliance tube is generally larger than an outer diameter of the catheter body so that the compliance tube freely extends and/or rotates with respect to the catheter body as the scoring structure foreshortens.

The compliance tube may also be sized to control the compliance of the scoring structure and expandable shell. Generally, the compliance tube has wall thickness ranging from 0.001 in to 0.1 in., preferably 0.005 in. to 0.05 in. The wall thickness may be increased to lessen the compliance of the system, or decreased to create a greater compliance. The length of the compliance tube may also be adjusted to control the compliance of the system. Generally, compliance tube has a length ranging from 1 cm to 10 cm, but may range up to 30 cm or more for embodiments wherein the tube extends across the length of the catheter body.

In most cases, the material of the compliance tube may also be selected to control the compliance of the scoring structure and expandable shell. Generally, the compliance tube comprises an elastic material, preferably a polymer such as nylon or Pebax™. Alternatively, the compliance tube may comprise a braided material, metal or wire mesh.

In some aspects of the present invention, the compliance tube may have one or more perforations to control the compliance of the scoring structure and expandable shell. Generally, the perforations comprise one or more slots extending along the outside circumference of the compliance tube. The slots may form a pattern along the outside circumference of the compliance tube. The slots may be parallel to each other, and/or extend helically or radially across the circumference of the compliance tube. The slots themselves may be formed of a variety of shapes, such as circular or rectangular.

Preferably, compliance tube has an outer diameter that tapers from its distal end to its proximal end so that the outside diameter at the proximal end is slightly larger than the inner diameter, and the outside diameter at the distal end is sized to approximate the diameter of the scoring structure when in a collapsed configuration. This allows for the catheter to be readily removed from a vessel without catching or snagging on the vessel wall. For the tapered configuration, the outer diameter of the compliance tube will vary depending on the size of the catheter body and the expansion cage, but the diameter generally tapers down in the range of 0.004 in to 0.010 in. from the distal end to the proximal end.

In another aspect of the invention, the attachment structure is connected at its distal end to the scoring structure and at its proximal end to a manipulator. Typically, the manipulator is positioned at the proximal end of the catheter body and the attachment structure extends from the scoring structure across the length of the catheter body. In all cases, the attachment structure is capable of axially and rotationally extending to accommodate foreshortening of the scoring structure as the shell is expanded.

In a preferred embodiment, the attachment structure comprises a compliance tube having an outer diameter and an inner diameter that extends over the catheter body. Typically, the inner diameter of the compliance tube is larger than an outer diameter of the catheter body so that the compliance tube freely extends and rotates with respect to the catheter body as the scoring structure foreshortens. The compliance of the scoring structure and expandable shell may be controlled by adjusting the thickness, length, or material selection of the compliance tube.

In some embodiments, the compliance of the scoring structure is controlled by actuating the manipulator during expansion or contraction of the radially expandable shell. Specifically, the attachment structure may be axially advanced with respect to the catheter body as the balloon is being inflated or deflated. For example, the attachment structure may be pulled away from the distal end of the catheter body while the balloon is being expanded to constrain the compliance of balloon. Alternatively, the manipulator may be used to rotate the attachment structure with respect to the catheter body to control the compliance of the balloon during transition.

In another embodiment of the present invention, a method of dilatating a stenosed region in a blood vessel comprises introducing a scoring structure carried over an expandable shell that is connected to a catheter body by an attachment structure, and expanding the scoring structure within a stenosed region within the blood vessel. In this method, the attachment structure axially and/or rotationally extends to accommodate foreshortening of the scoring structure as the shell is expanded. The attachment structure generally comprises a compliance tube having an outer diameter and an inner diameter that extends over the catheter body, wherein the inner diameter of the compliance tube is larger than an outer diameter of the catheter body so that the compliance tube freely extends and rotates with respect to the catheter body as the scoring structure foreshortens. The thickness, length, and material of the compliance tube may be selected to control the compliance of the scoring structure and expandable shell.

In some embodiments, the method further comprises the step of fixing the proximal end of the attachment structure to the catheter body. Alternatively, the method may comprise the step of fixing the proximal end of the attachment structure to a manipulator. In such an embodiment, manipulator is positioned at the proximal end of the catheter body and the attachment structure extends from the scoring structure across the length of the catheter body. This allows for the compliance of the scoring structure and balloon to be controlled by actuating the manipulator during expansion or contraction of the radially expandable shell. Actuation of the manipulator may occur by axially advancing, pulling or rotating the attachment structure with respect to the catheter body.

BRIEF DESCRIPTION OF THE DRAWINGS

FIG. 3 is a schematic illustration of an expanded angioplasty balloon carrying a helical scoring structure in accordance with embodiments of the invention.

FIG. 10 illustrates an alternative embodiment of a helical scoring structure comprising serpentine and zigzag structures for mounting onto a balloon catheter.

FIG. 11 illustrates a first of the serpentine mounting elements of the scoring structure of FIG. 10.

FIG. 12 illustrates a second of the serpentine mounting elements of the scoring structure of FIG. 10.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the present invention relate to device for revascularization of stenotic vessels and specifically to a balloon catheter having external elements. The dilatation device comprises a conventional dilatation balloon such as a polymeric balloon and a spiral, or external elements with other configurations mounted on the balloon catheter.

Figure 1:
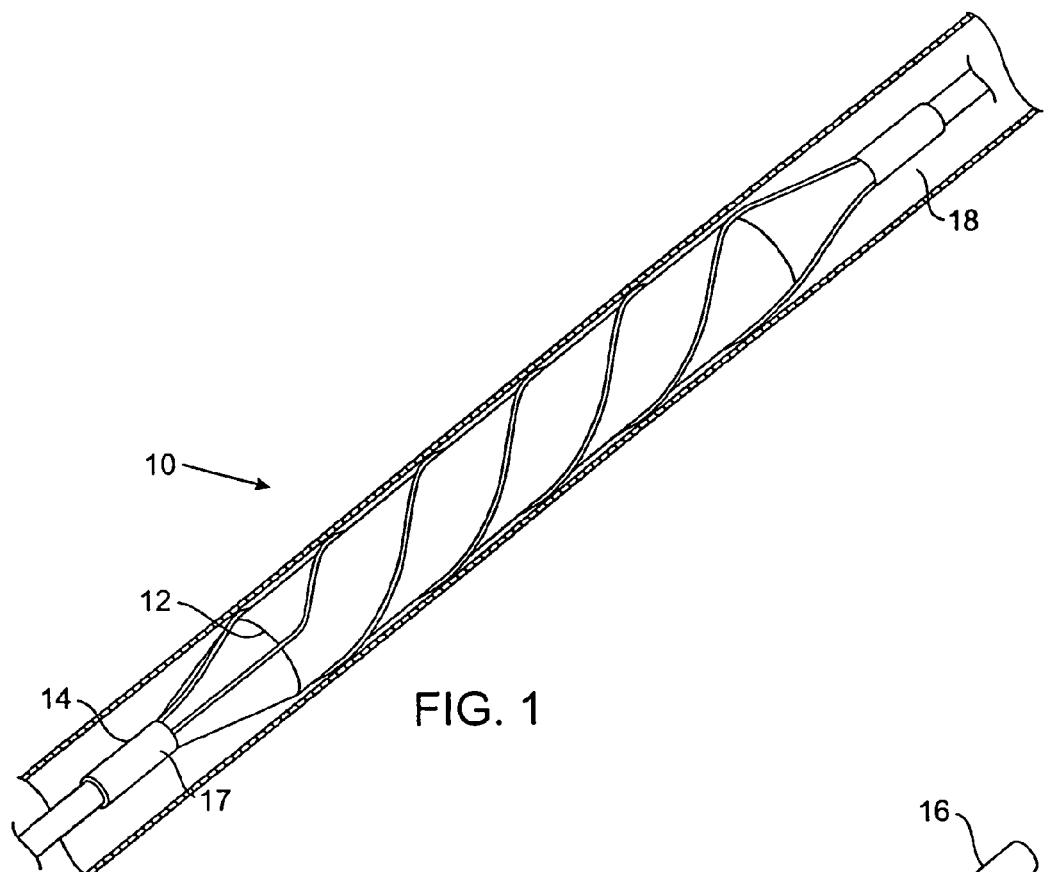
FIGS. 1, 1A, 1B and 1C are schematic illustrations of the balloon scoring structure embodiment in accordance with an embodiment of the invention.
Figure 1A:
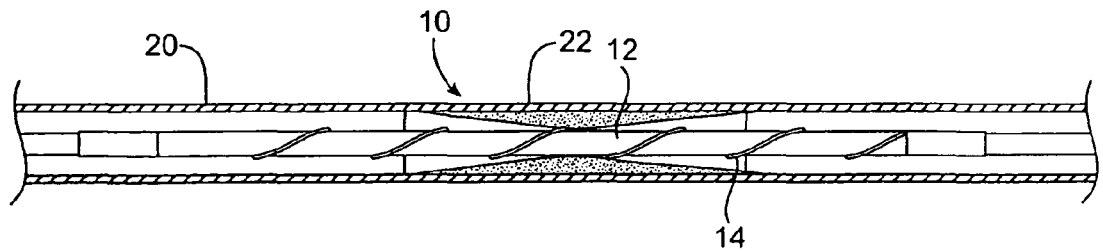
Figure 1B:
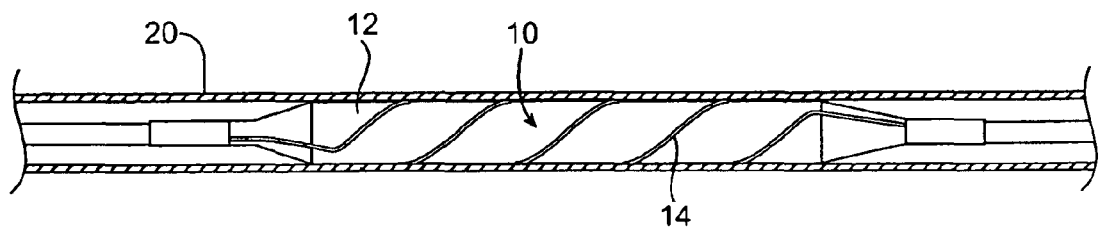

Reference is now made to FIGS. 1, 1A and 1B, which are schematic illustrations of a dilatation device 10 in accordance with embodiments of the invention. The dilatation device 10 includes a dilatation balloon 12, which may be any conventional angioplasty balloon such as commonly used by interventional cardiologists or radiologists, and a helical or spiral unit 14 mounted over or attached to dilatation balloon 12. The compliance of the balloon and the scoring element(s) should be chosen to assure uniform expansion of the balloon substantially free from "dog-boning" as the combined structure expands within a lesion. If a compliant or a semi-compliant balloon is used and the compliance of the scoring element was not matched to comply with the properties of the balloon, the expansion of the balloon-scoring element system will not be uniform. This non-uniformity may impair the efficacy of the scoring catheter and, in some cases, may result in poor performance. For example, under given pressure, certain parts of the balloon will be able to expand while other parts will be constrained by excessive resistance of the scoring elements.

Helical unit 14 typically made of nitinol. Helical unit 14 may be made of other metals such stainless steel, cobalt-chromium alloy, titanium, and the like. Alternatively, spiral unit 14 may be a polymeric spiral, or made of another elastic material. Helical unit 14 may be attached at its proximal and distal ends to the proximal end 17 and distal end 18 of dilatation balloon 12. Alternatively, spiral unit 14 may be attached to the distal end and/or the proximal end of dilatation balloon 12 by collar-like attachment elements 15 and 16. Spring or other compliant elements may be alternatively or additionally provided as part of the attachment elements to accommodate shortening of the helical unit as it is expanded.

Dilatation device 10 is inserted into the vascular system, for example, using a conventional catheter procedure, to a region of stenotic material 22 of blood vessel 20. (The term "stenotic" is used herein to refer to the vascular lesion, e.g., the narrowed portion of the vessel that the balloon is meant to open.) At the stenotic area, the dilatation balloon 12 is inflated, for example, by liquid flow into the balloon. Helical unit 14 widens on the inflated dilatation balloon 12. On inflation, the dilatation balloon 12 together with the helical unit 14 is pressed against the walls of blood vessel 20 as shown in FIG. 1B.

Figure 1C:
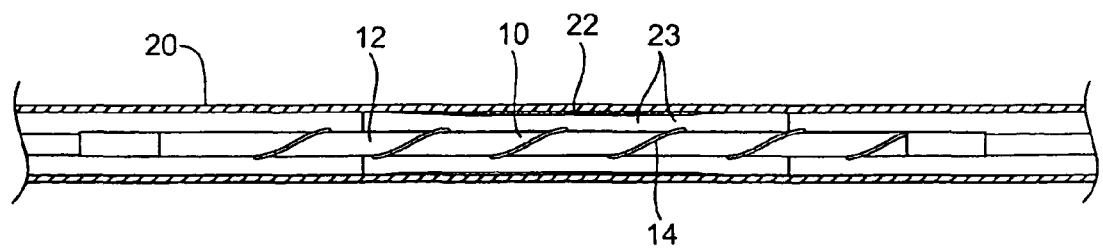

Reference is now made to FIG. 1C, illustrating blood vessel 20 after the deflation of dilatation balloon 12. Helical unit 14 narrows when deflating the dilatation balloon 12, thus the dilatation device 10 is narrowed and may be readily retrieved from blood vessel 20. The deflation profile of the balloon 10 is low and mainly circular. The stenotic material 22 in blood vessel 20 is pressed against blood vessel 20 walls to widen the available lumen and enhance blood flow. The pressing of helical unit 14 against the walls of blood vessel 20 causes scoring 23 in the stenotic area.

Reference is now made to FIG. 3 that shows a scoring structure in the form of a single wire 24 wrapped around a dilatation balloon 12 in a helical configuration.

In other embodiments, the scoring structure of the present invention can have a non-helical configuration. Any design of scoring structure that can accommodate an increase in the diameter of the balloon 12 upon inflation, and return to its configuration when the balloon is deflated, is an appropriate design useful in the invention. At least a portion of the scoring elements will not be parallel to the longitudinal axis of the balloon catheter to enhance flexibility and improve scoring.

Referring again to FIGS. 1A-1C, helical unit 14 is pushed outwardly by the inflation of the balloon 12, and is stretched by the inflation of the balloon. When the balloon is deflated, helical unit 14 assists in the deflation by its elastic recoil. This active deflation is faster and also leads to a low profile of the deflated balloon. The balloon 12 is disposed within the helical unit 14, which returns to its pre-inflated shape and forces the balloon to gain a low radial profile.

In another embodiment of the invention, dilatation device 10 may carry a stent. The stent can be crimped over the helical unit 14. In this way, the helical unit 14 can push the stent against hard areas of the lesion, enabling proper positioning of the stent against the vessel wall, even in hard-calcified lesions without pre-dilation.

Figure 2:
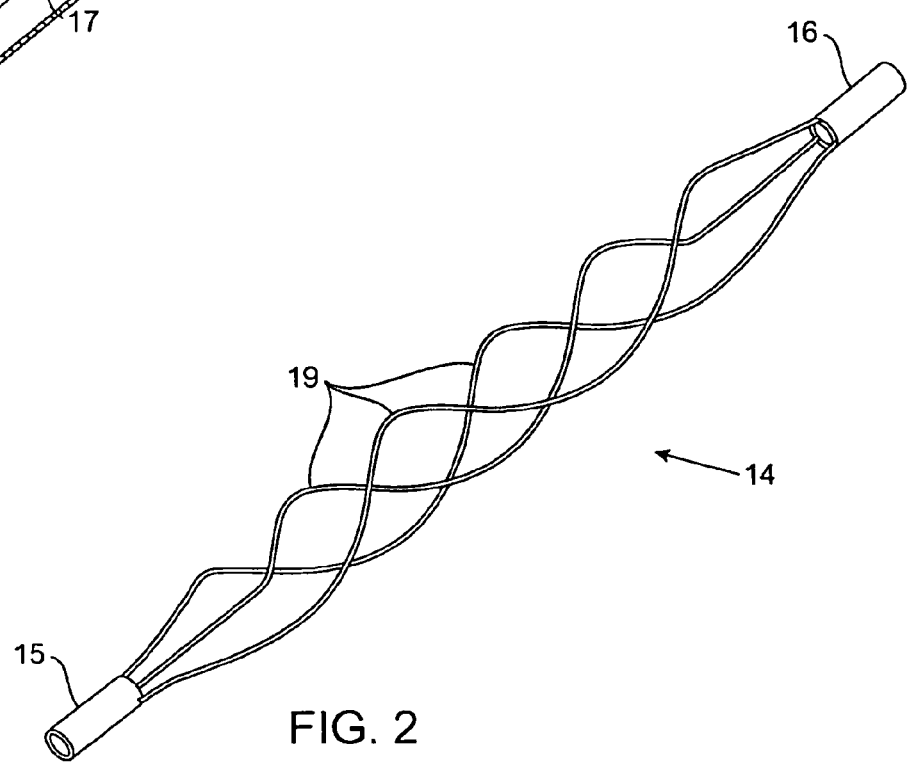
FIG. 2 is a schematic illustration of an exemplary helical scoring structure embodiment in accordance with embodiments of the invention.

Reference is now made to FIG. 2, illustrating the helical unit 14 in accordance with embodiments of the invention. Helical unit 14 is typically made of nitinol. Helical unit 14 includes three wires 19 that are attached to collars 15 and 16 at the proximal end and distal end, respectively. Alternatively the scoring structure may be formed as a metallic cage, which can be made from a slotted tube, or polymeric cage or polymeric external elements. Alternatively the scoring structure may comprise wires of other elements attached directly to the balloon material or close to the balloon ends.

Wires 19 (FIG. 2) are attached between collars 14 and 15. The diameter of the wires is typically in the range of 0.05 mm to 0.5 mm. Alternatively, a cage (for example a metallic cage made of a slotted tube) can be used in several configurations that allow local stress concentrations. The size and shape of the cross section of the cage elements or the cross section of the wires can vary. The cross section can be a circle, rectangle, triangle, or other shape.

In alternative embodiments, the wires 19 may comprise short segments that are attached to the balloon 12.

In further alternative embodiments of the invention, the helical unit 14 may be glued, thermally bonded, fused or mechanically attached at one or both ends to dilatation balloon 12.

In yet another embodiment, a scoring structure may comprise wires that are attached to the dilatation balloon 12 in helical configuration or other configuration. The wires may be thermally attached to the balloon 12, glued, mechanically attached, or the like.

In still another embodiment, a scoring structure comprises wire or cage elements that are not parallel to the longitudinal axis of the balloon 12 so that the combination of the scoring structure 19 and the balloon 12 remains flexible.

In additional embodiments, the combination of dilatation balloon 12 and scoring structure scores the lesion and provides better vessel preparation for drug eluting stents by allowing better positioning of the stent against the vessel wall and diffusion of the drug through the scores in the lesion.

In these embodiments, the balloon can be used as a platform to carry drugs to the lesion where scoring of the lesion can enhance delivery of the drug to the vessel wall.

In these embodiments, the balloon can be used for a local drug delivery by embedding drug capsules, drug containing polymer, and the like, through the stenotic material and into the vessel wall.

From the above, it can be seen that the invention comprises catheters and scoring structures, where the scoring structures are positioned over the balloons or other expandable shells of the catheter. The scoring structures may be attached directly to the balloons or other shells, in some cases being embedded in the balloon material, but will more usually be formed as separate cage structures which are positioned over the balloon and attached to the catheter through attachment elements on either side of the balloon. The expandable cages may be formed using conventional medical device fabrication techniques, such as those used for fabricating stents, such as laser cutting of hypotube and other tubular structures, EDM forming of hypotubes and tubes, welding of wires and other components and the like.

Typically, such expandable shell structures will comprise the attachment elements and an intermediate scoring section between the attachment elements. As illustrated in the embodiments above, the attachment elements may be simple cylindrical or tube structures which circumscribe the catheter body on either side of the balloon or other expandable shell. The simple tube structures may float over the catheter body, i.e., be unattached, or may be fixed to the catheter body. A number of alternative embodiments for the attachment elements will be described in connections with the embodiments below.

The intermediate scoring sections may also have a variety of configurations where at least some of the scoring elements will typically be disposed in a non-axial configuration, i.e., in a direction which is not parallel to the axial direction of the expandable cage. A preferred configuration for the intermediate scoring section comprises one or more helical elements, generally as illustrated in the prior embodiments. Other exemplary configurations are set forth in the embodiments described below.

Figure 4:
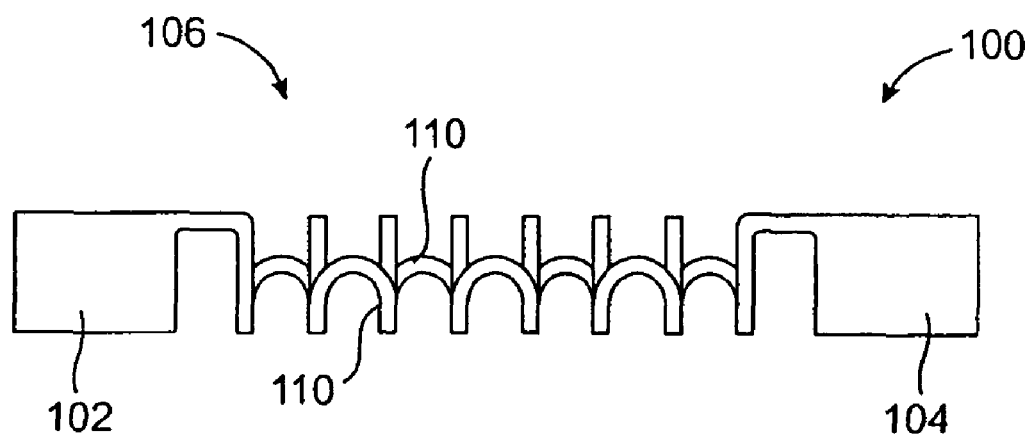
FIG. 4 illustrates a scoring structure comprising an alternating serpentine pattern of intermediate scoring elements between a pair of end collars.
Figure 5:
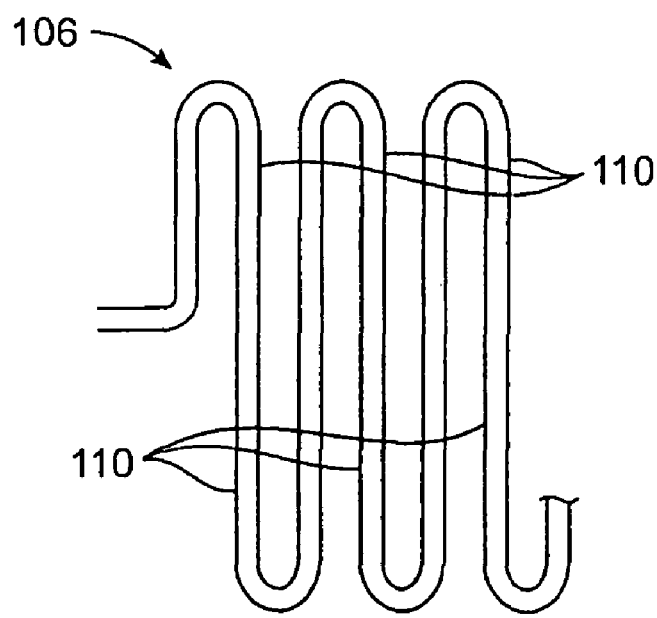
FIG. 5 illustrates the serpentine scoring elements of the embodiment of FIG. 4 showed in a rolled-out configuration.
Figure 6:
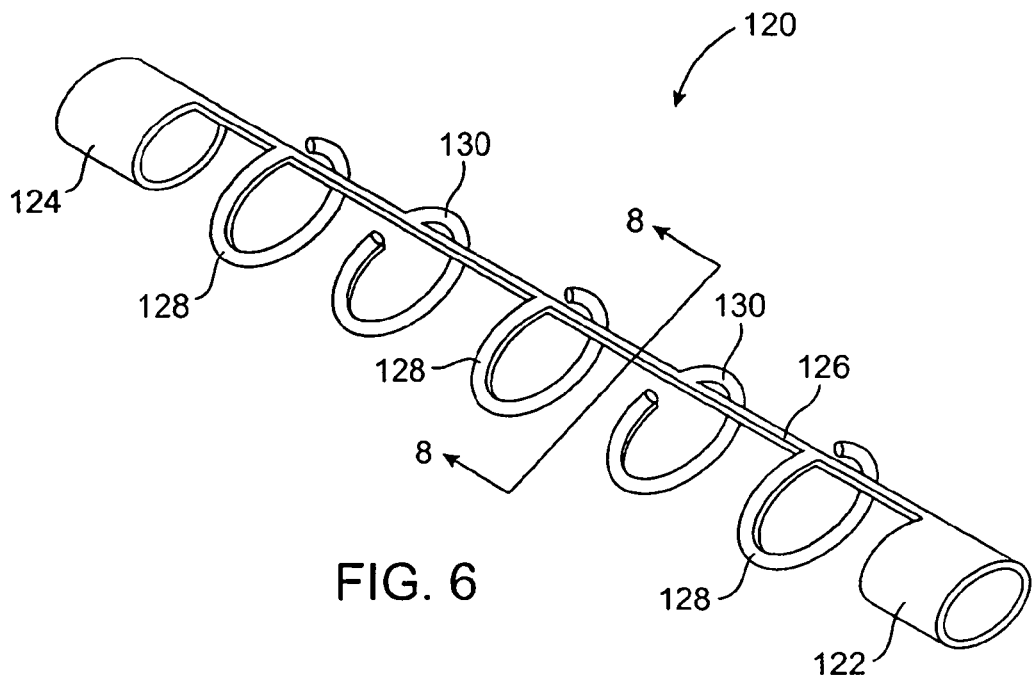
FIG. 6 illustrates a scoring structure comprising alternating C-shaped scoring elements between a pair of end collars.
Figure 7:
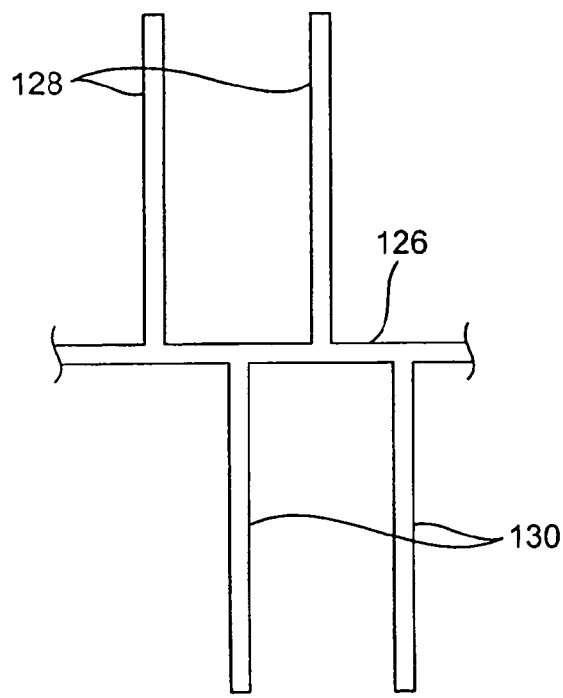
FIG. 7 illustrates the C-shaped scoring elements of the embodiment of FIG. 6 shown in a rolled-out configuration.
Figure 8:
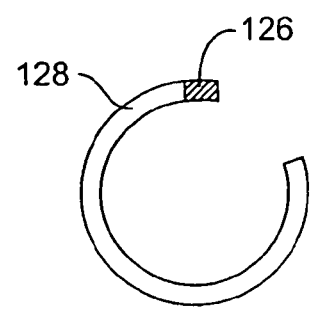
FIG. 8 is a view of one of the C-shaped scoring elements taken along line 8-8 of FIG. 6.

Referring now in particular to FIGS. 4 and 5, an expandable scoring cage 100 comprises first and second attachment elements 102 and 104, respectively, and an intermediate scoring section 106 comprising a plurality of curved serpentine members 110. The serpentine members 110 extend circumferentially in opposite directions in an alternating manner. This can be understood by observing a "rolled-out" view of the serpentine elements as illustrated in FIG. 5. A second alternative scoring cage structure 120 is illustrated in FIGS. 6-8. The scoring cage 120 comprises first and second attachment elements 122 and 124 joined by a spine 126. Plurality of C-shaped scoring elements 128 and 130 are attached to the spine and extend in opposite circumferential directions. The shape of the element can be observed in FIG. 8. The opposite directions may be observed in the rolled-out view of FIG. 7.

Figure 9:
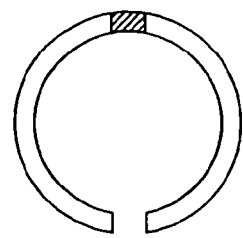
FIG. 9 illustrates an alternative double C-shaped scoring element which could be utilized on a scoring structure similar to that illustrated in FIG. 6.

It will be appreciated that a variety of different circumferential structures may be used in place of the C-shaped structures of FIGS. 6-8. For example, a pair of opposed C-shaped partial ring structures may be utilized, as illustrated in FIG. 9. The C-shaped structures of FIG. 6 or the double C-shaped structures of FIG. 9 can also be extended so that they wrap around a balloon more than one time, either over or under the spine structure 126.

The expandable cage structures 100 and 120 will each be mounted over a dilatation balloon, such as the balloon of FIGS. 1-3, with the attachment elements secured to the catheter body on either side of the dilatation balloon. The tube or cylindrical attachment elements 102, 104, 122, and 124 may simply float over the catheter body. In other embodiments, however, it may be desirable to use an adhesive or other means for affixing either one or both of the attachment elements to the catheter body. Having at least one floating attachment element, however, is often desirable since it can accommodate shortening of the intermediate scoring section as that section radially expands. In other cases, however, the individual scoring elements may possess sufficient elasticity to accommodate such shortening. For example, nitinol and other shape memory alloys possess significant stretchability, typically on the order of 8% which in some instances will be sufficient to accommodate any tension applied on the intermediate scoring section by radial expansion of the balloon.

Referring now to FIGS. 10-12, alternative attachment elements are shown on an embodiment of an expandable scoring cage 140 comprising three helical scoring elements 142 which make up the intermediate scoring section. A first attachment element 146 comprises a single serpentine ring, as best illustrated in FIG. 11 while a second attachment element 148 comprises a pair of tandem serpentine rings 150 and 152, as best illustrated in FIG. 12. The use of such serpentine attachment structures is beneficial since it permits crimping of either or both of the structures onto the catheter body in order to fix either or both ends of the structure thereto. Usually, the single serpentine attachment structure 48 will be affixed to the catheter body while the double serpentine structure will be left free to allow movement of that end of the scoring cage to accommodate radial expansion of the underlying balloon.

Figure 13:
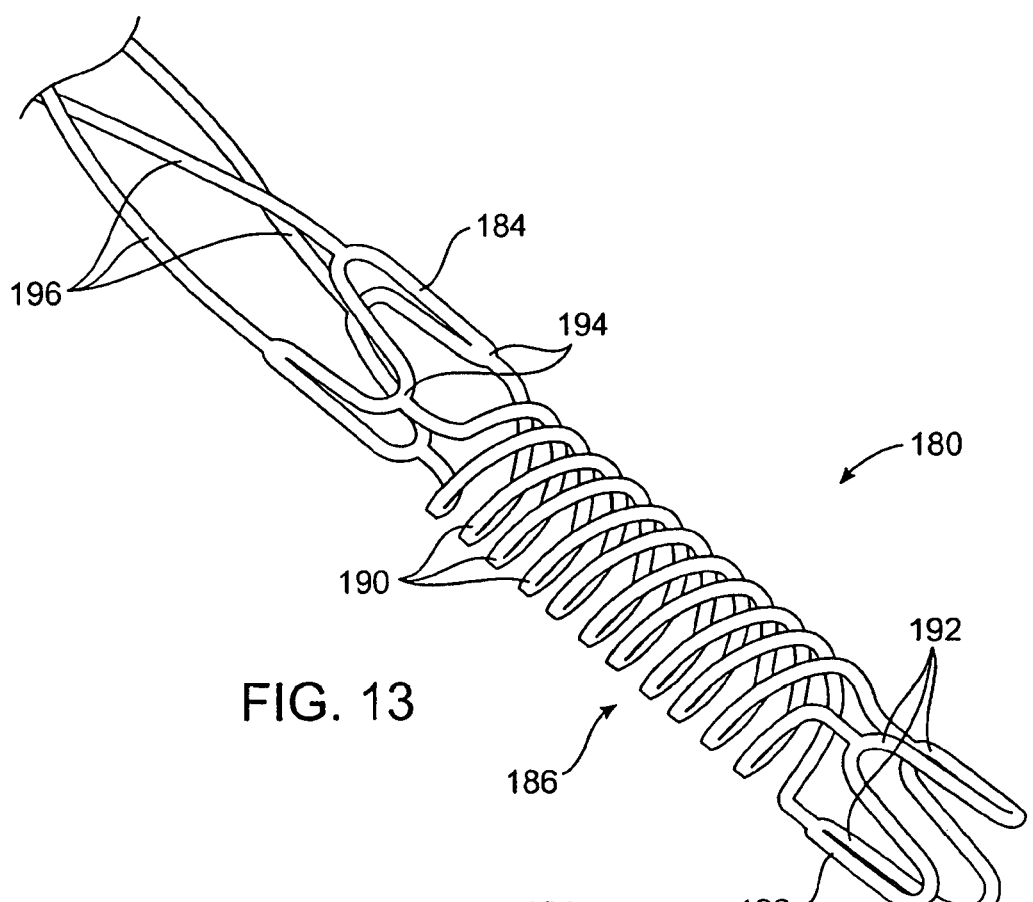
FIG. 13 illustrates an alternative mounting structure for a helical or other scoring structure.
Figure 14:
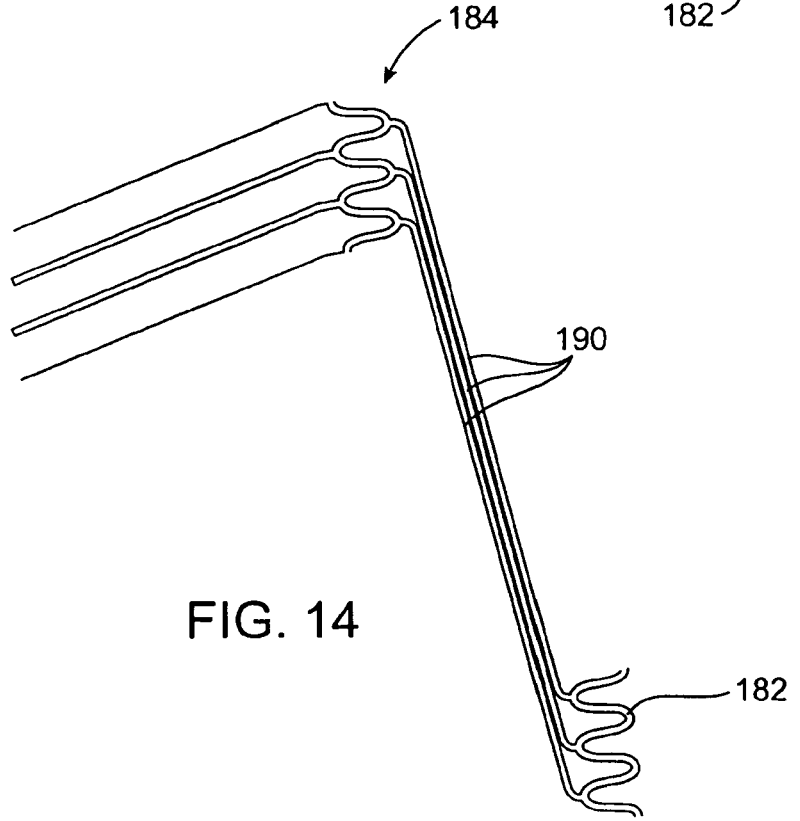
FIG. 14 illustrates the mounting structure of FIG. 13 shown in a rolled-out configuration.

Referring now to FIGS. 13 and 14, a further alternative embodiment of an attachment element useful in the scoring cages of the present invention is illustrated. Attachment element 180 includes a pair of serpentine rings 182 and 184, generally as shown in FIG. 12, in combination with a coil spring structure 186 located between said rings 182 and 184. The coil spring structure 186 includes three nested coil springs 190, each joining one of the bend structures 192 and 194 on the serpentine rings 182 and 184, respectively. The structure of the spring structure and adjacent serpentine rings can be understood with reference to the rolled-out configuration shown in FIG. 14.

The attachment structure 180 is advantageous since it permits a fixed attachment of the outermost ring 182 to the underlying catheter body while the inner ring 184 remains floating and expansion and contraction of the intermediate scoring section, comprising helical elements 196, is accommodated by the coil spring structure 186. Since the scoring cage is fixed to the catheter, any risk of loss or slippage from the balloon is reduced while sufficient compliance is provided to easily accommodate radial expansion of the intermediate scoring section. By attaching the structures 180 at at least one, and preferably both ends of the scoring cage, the risk of interference with a stent is reduced.

In some embodiments, collars, such as those shown in FIGS. 1 and 2, or attachment elements, such as those shown in FIGS. 10-12, may comprise a flexible material that allows the collar or attachment element to expand while being mounted over the balloon catheter and then be collapsed to the diameter of the catheter. The expandability of the collars and/or attachment elements may be achieved by a compliant memory material such as nitinol or a polymer, or by use of a flexible serpentine design as shown in FIGS. 10-12. Where collars are used, the collar may be shaped or have a slit down the circumference (not shown) so that the collar may be expanded during mounting over the balloon. Alternatively, the collar may be oversized to accommodate the balloon diameter mounting, and then crimped down to secure the secure the scoring structure to the catheter body.

Figure 15:
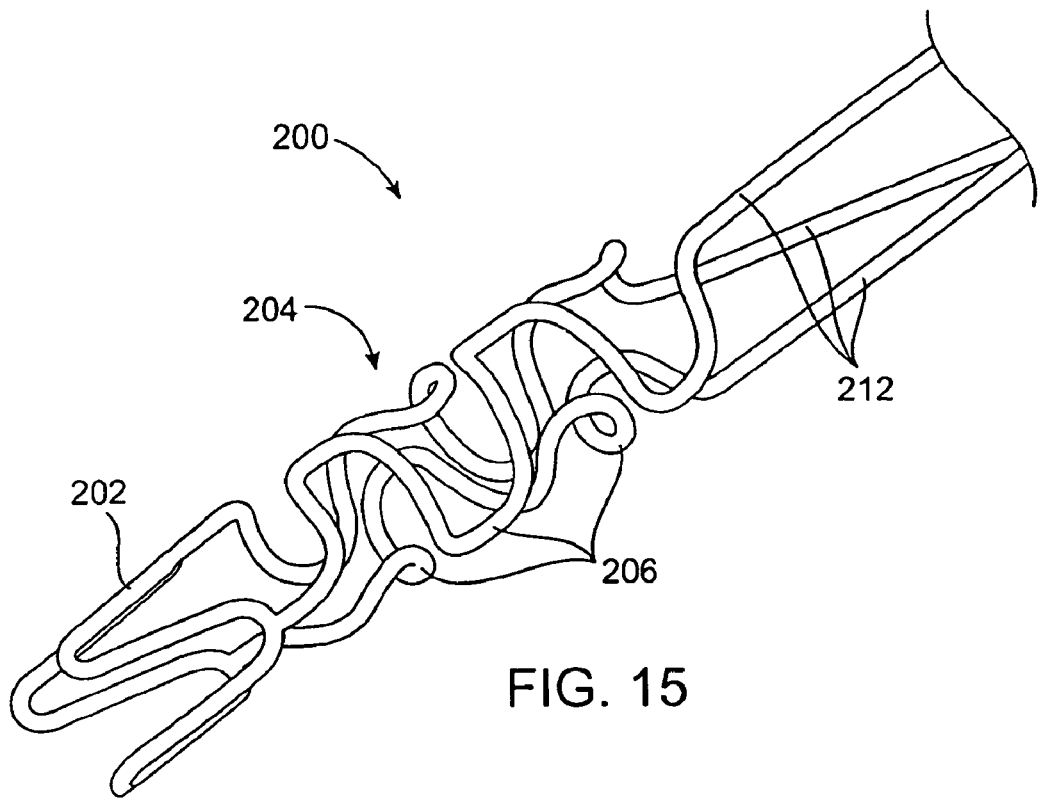
FIG. 15 shows yet another embodiment of a mounting element for the scoring structures of the present invention.
Figure 16:
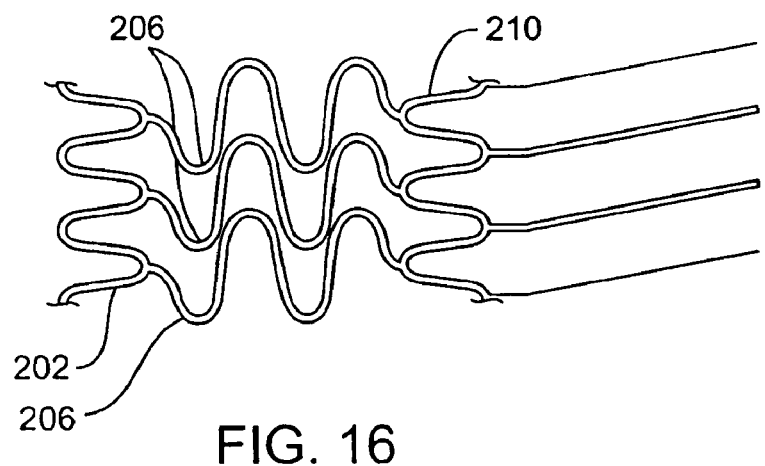
FIG. 16 illustrates the mounting structure of FIG. 15 shown in a rolled-out configuration.

Yet another embodiment of the attachment element of the present invention includes an axial spring as shown in FIGS. 15 and 16. The attachment element 200 includes a terminal serpentine ring 202 and an intermediate spring structure 204 including a number of axial serpentine spring elements 206. The nature of the serpentine ring elements 206 can be observed in the rolled-out configuration of FIG. 16. Optionally, a second serpentine ring 210 may be provided between the attachment structure 200 and the helical scoring elements of the intermediate scoring section 212.

The embodiments of FIGS. 13-16 comprise spring-like elements 186 and 204 to accommodate axial shortening of the scoring structure upon radial expansion. It will be appreciated that other metal and non-metal axially extensible structures could also be used in such attachment structures. For example, elastic polymeric tubes could be attached at one end to the scoring structures and at another end to the catheter body (or to a ring, collar or other structure which in turn is fixed to the catheter body).

Figure 17A:
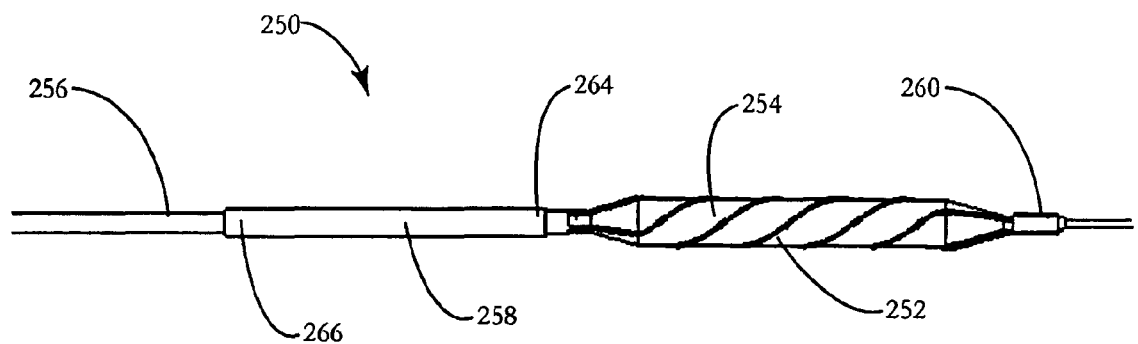
FIG. 17a illustrates yet another alternative embodiment of a catheter constructed in accordance with the principles of the present invention, where an attachment structure is disposed between the scoring structure and the catheter body.
Figure 17B:
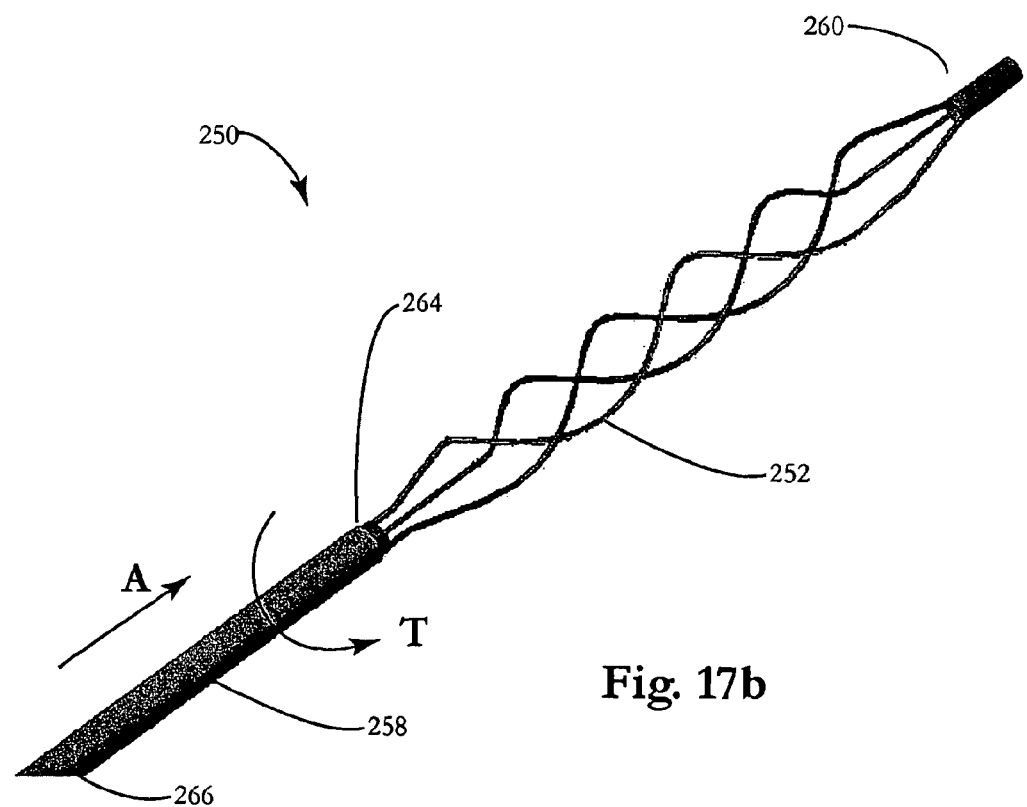
FIG. 17b illustrates the structure of FIG. 17a shown without the balloon.

Referring now to FIGS. 17a and 17b, a further embodiment of an angioplasty catheter 250 having an axially distensible attachment structure 258 is illustrated. External structure 252 is held over expandable dilatation balloon 254 and is fixed at one end to the distal end 260 of catheter body 256. The external structure may comprise any structure typically used for removal of plaque/thrombus from a vessel wall such as a scoring structure, cutting structure or crushing structure. The proximal end 262 of external structure 252 is connected to the distal end 264 of attachment structure 258. The proximal end 266 of attachment structure 258 is fixed to the catheter body 256. As described below, the attachment structure 258 may be configured to reduce forces applied on the external structure 252 and the catheter body 256 during expansion and contraction of balloon 254.

In a preferred embodiment, attachment structure 258 comprises a cylindrical over-tube, or compliance tube, made of an elastic material. Over-tube 258 generally has an inner diameter that is slightly greater than the outer diameter of the catheter body 256. Because only a small section of the proximal end of the attachment structure 258 is fixed to the catheter body, the distal end 264 attached to external structure 252 is free floating, and is free to slide axially and rotationally with respect to catheter body 256. Attachment structure 252 may be fixed, for example by adhesion, directly to the to catheter body 256 and external structure 252, or to a collar or other intermediate attachment means.

As balloon 254 is expanded, external structure 252 expands in circumference and contracts axially along the catheter body 256, creating axial force A on attachment structure 258. Attachment structure 258, fixed to the catheter at its end 266, axially stretches to accommodate the axial movement of the external structure 252. External structure 252 also tends to rotate about the catheter body 256, causing a torsional force T. The distal end 264 of attachment structure 258 rotates through the full range of motion of scoring structure 252 to accommodate torsional force T, while proximal end 266 remains stationary with respect to catheter body 256.

The configuration illustrated in FIGS. 17a and 17b allows the compliance of the expandable system to be controlled. Generally, where one end of the scoring structure is free, the compliance of the expandable system will be a combination of the compliance of the balloon and the scoring structure. However, because the ends of the expandable system shown in FIG. 17 are fixed at distal end 260 and proximal end 266, the attachment structure controls the compliance of the expandable system.

The compliance of the system may be varied by any combination of material selection, wall thickness, or length of the over-tube 258. Over-tube 258 may comprise any elastomer, such as elastic polymer like Nylon, Pebax, or PET. Typically, compliance tube 258 is formed from extruded tubing, but is may also comprise braided polymeric or metallic fibers, or wire mesh. A high memory metal such as nitinol or stainless steel may also be used. Where the compliance tube comprises an extruded polymeric tube, the wall thickness can vary in the ranges set forth above, and the length of the tube can range from 1 cm to 10 cm. For the same material, the thinner-walled and longer the tube, the more compliant the system.

Figure 18A:
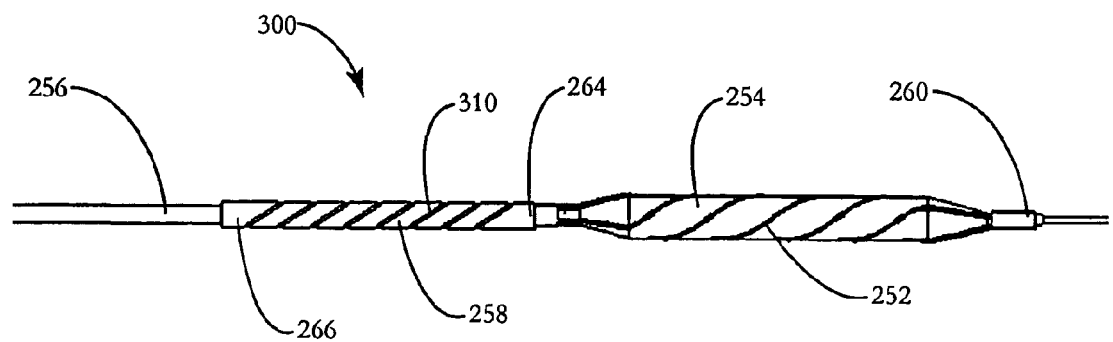
FIGS. 18a-c illustrate a catheter constructed in accordance with the principles of the present invention having an attachment structure with various patterned perforations.
Figure 18B:
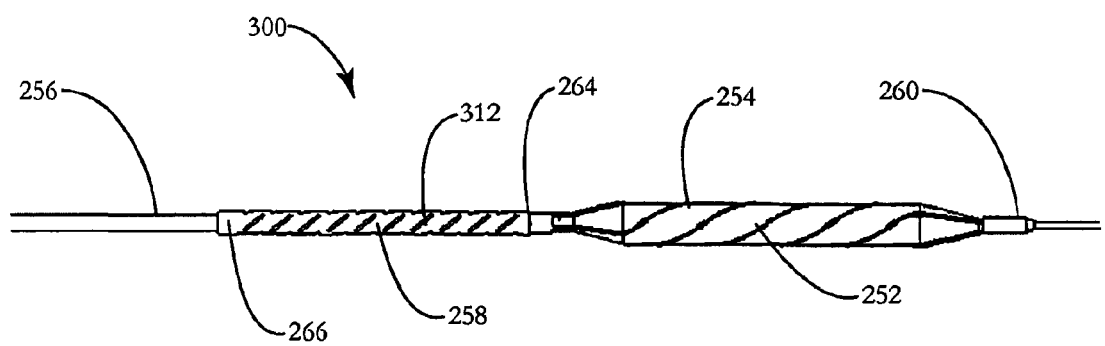
Figure 18C:
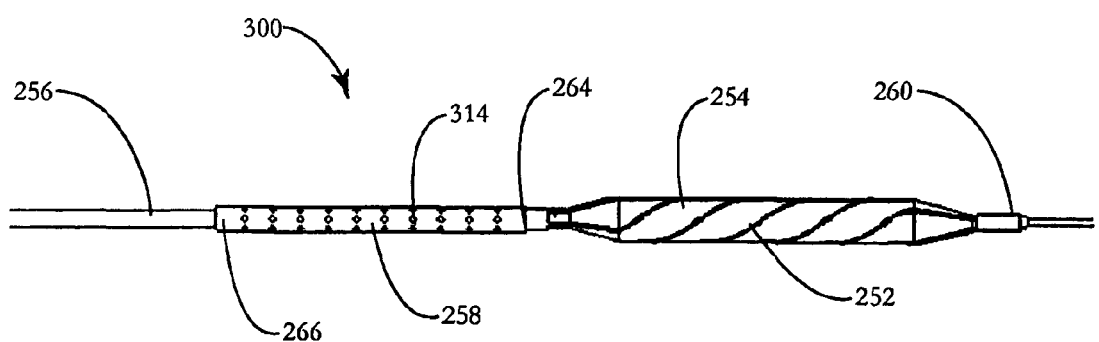

Referring to FIGS. 18a-c, the compliance of a angioplasty catheter 300 may also be varied by creating one or more perforations in compliance tube 258. The perforations may comprise one or more slots in the circumference of the tubing. The slots may comprise one continuous slot spiraling across the length of compliance tube 258, or may be a number of slots aligned in any number of patterns, such as helical 312, or radial 314. The slots may also be any number of shapes, such as circular or rectangular, and may have a discreet length or be contiguous across the surface of the compliance tube.

Figure 19:
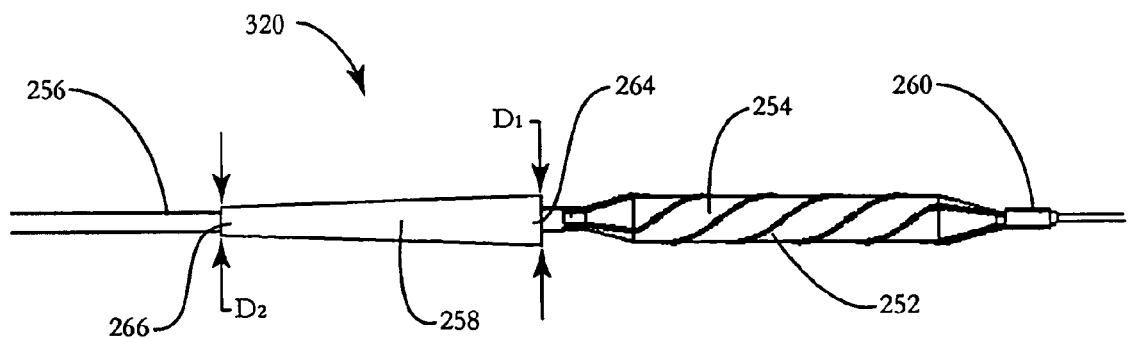
FIG. 19 illustrates another embodiment of a catheter constructed in accordance with the principles of the present invention having a tapered attachment structure.

Referring to FIG. 19, the outside diameter of compliance tube 258 may be tapered to facilitate delivery and retrieval of the scoring catheter 320 from the treatment site within the lumen. Generally, the outer diameter will be larger at the distal end 264 of the compliance tube 258 and smaller at the proximal end 266 of the compliance tube. The outside diameter $D_1$ at the distal end will vary depending on the profile of the scoring structure and balloon when collapsed but typically range from 0.004 in. to 0.01 in. larger than the outside diameter $D_2$ at the proximal end. The outside diameter $D_2$ at the proximal end is generally as close as possible to the outside diameter of the catheter body to create a smooth transition between the compliance tube and the catheter. As an example, for a catheter body having an outside diameter of 0.033 in., outside diameter $D_1$ at the distal end may be 0.042 in. with an inner diameter of 0.038 in., the inner diameter providing clearance between the catheter body so that the distal end of the compliance tube can move relative to the catheter body. Correspondingly, the outside diameter $D_2$ at the proximal end may taper down to 0.0345 in., with an inner diameter of 0.034 in. to closely match the catheter body having outside diameter with enough clearance to be bonded to the catheter body by an adhesive.

The taper may run across the whole length of the compliance tube, or alternatively be only tapered at a section of the length of the compliance tube. The tapered compliance tube 258 smoothes the transition between the scoring structure and catheter body, and minimizes the likelihood of the outer tube or scoring structure snagging or catching on a portion of the luminal wall during delivery or retrieval of the catheter.

Figure 20:
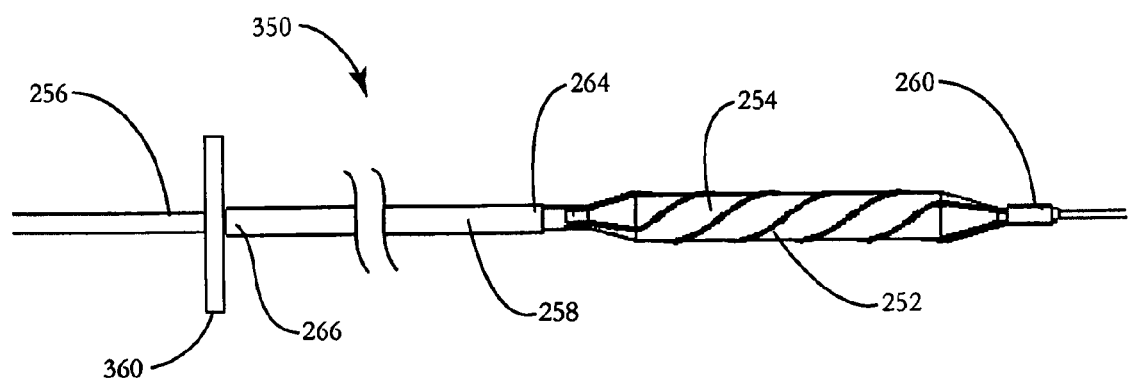
FIG. 20 illustrates yet another alternative embodiment of a catheter constructed in accordance with the principles of the present invention, where an attachment structure is connected to a manipulator.

Now referring to FIG. 20, an alternative embodiment of a scoring catheter 350 is shown having a manipulator 360. The attachment structure 258 is connected at its distal end 264 to the scoring structure 252. Instead of being secured directly to the catheter body 256, the proximal end 266 is attached to manipulator 360. Typically, the manipulator 360 is positioned at the proximal end of the catheter body 256 and the attachment structure 258 extends from the scoring structure across the length of the catheter body. Like the above embodiments, the attachment structure is capable of axially and rotationally extending to accommodate foreshortening of the scoring structure as the shell is expanded.

In some embodiments, the compliance of the scoring structure 252 and balloon 254 is controlled by actuating the manipulator during expansion or contraction of the radially expandable shell. In one aspect, the attachment structure 258 may be axially advanced with respect to the catheter body 256 as the balloon is being inflated or deflated. For example, the attachment structure 258 may be pulled away from the distal end of the catheter body 256 while the balloon 254 is being expanded to constrain the compliance of balloon. The attachment structure 258 may also be pulled away from the distal end of the catheter body 256 during or after the balloon 254 is being deflated to minimize the profile of the balloon and scoring structure. Alternatively, the manipulator 360 may be used to rotate the attachment structure 258 with respect to the catheter body 256 to control the compliance of the balloon and scoring structure during transition from a collapsed to expanded state and back to a collapsed state.

Figure 21:
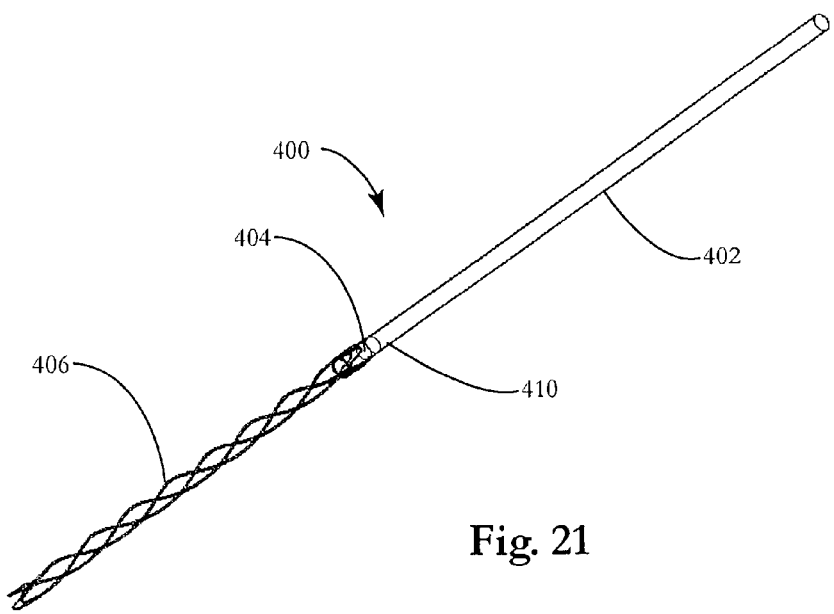
FIG. 21 illustrates an embodiment of the invention having a laminated section at the distal end of the compliance tube.
Figure 22:
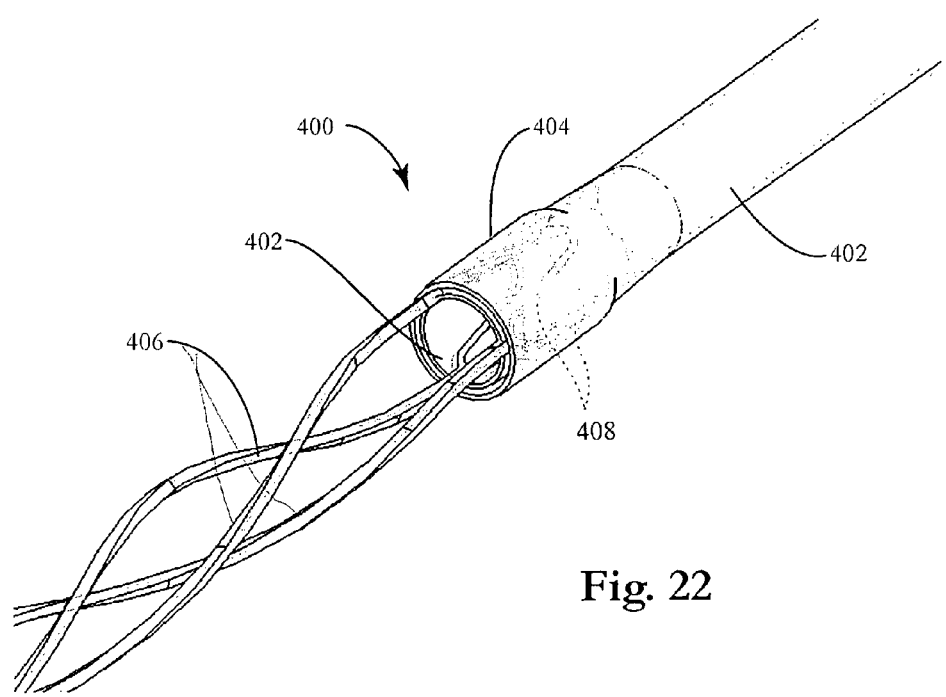
FIG. 22 illustrates another view of the embodiment of FIG. 21.

Now referring to FIGS. 21 and 22, a scoring cage structure 400 is illustrated having a two-layer laminated compliance tube 402. As shown in FIG. 22, the compliance tube 402 has a laminated structure 404 at at least its distal end 410. The laminated structure holds the proximal ends 408 of the scoring elements 406 as shown in broken line in FIG. 22. The scoring elements 406 may be sized to fit over the outside of the compliance tube 402, as illustrated in FIG. 22, with the lamination covering the elements. Alternatively, the compliance sleeve tube 402 may be sized to fit inside of the scoring structure 406, with the laminating layer(s) formed over the elements 406 (not shown).

The laminating structure may be composed of a polymer similar to the compliance tube 402, and may be heat shrunk or melted to thermally bond the compliance sleeve to the compliance tube and sandwich the scoring structure 406. Alternatively, an adhesive or other bonding method such as ultrasonic or RF energy may be used to laminate the structure. The laminated structure as shown in FIGS. 21 and 22, provides a smoothed transition and strengthened bond between the scoring cage and the attachment structure. Such a smooth transition is a particular advantage when withdrawing the scoring cage from the vasculature.

Figure 23:
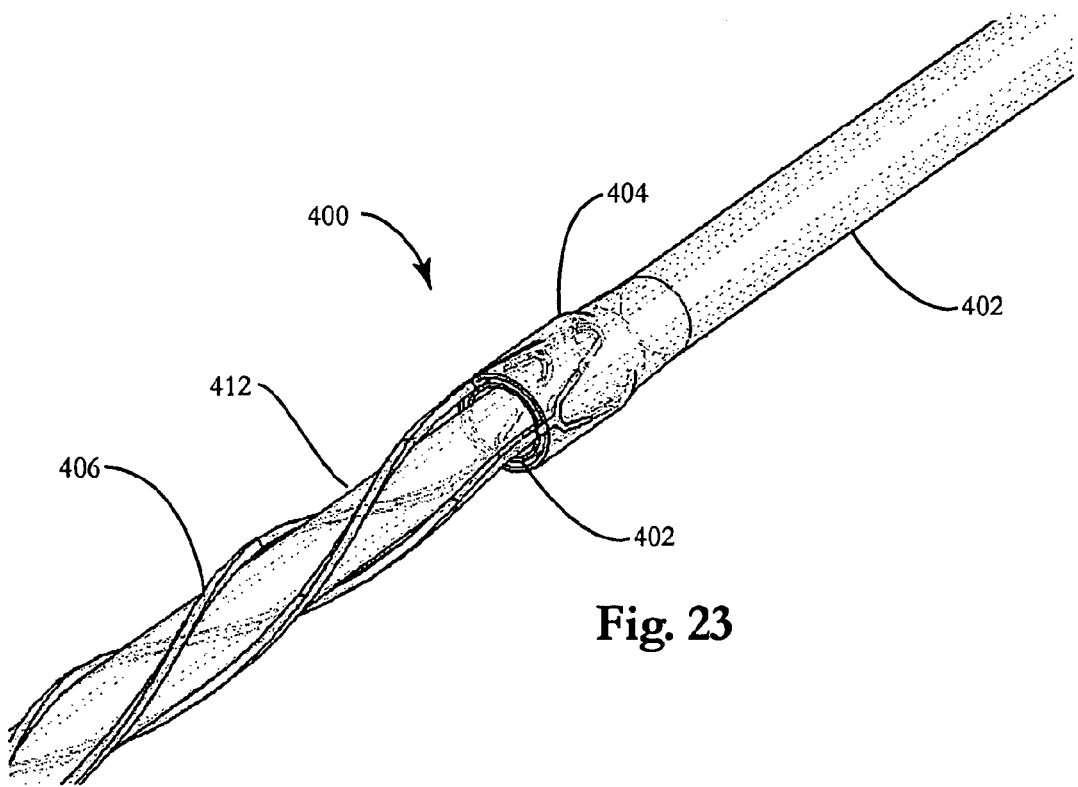
FIG. 23 illustrates the embodiment of FIG. 21 with an expandable balloon inserted within the scoring structure.
Figure 24:
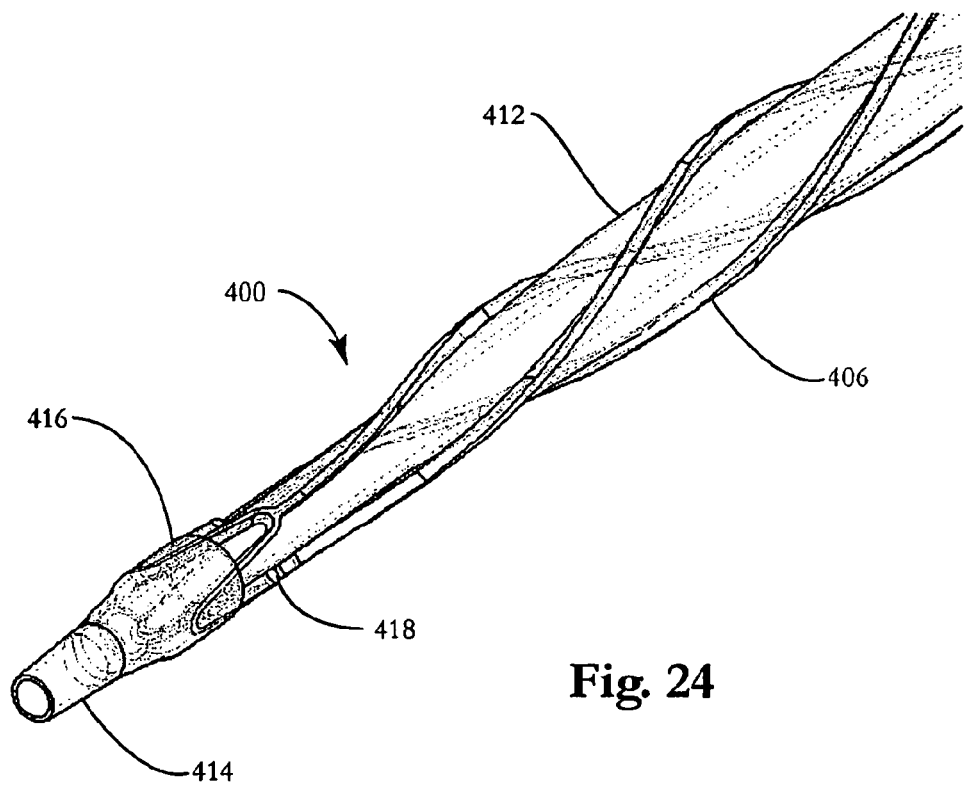
FIG. 24 illustrates an embodiment with a sleeve over the distal end of the scoring structure.

FIGS. 23 and 24 illustrate scoring cage 400 positioned over an expandable dilation balloon 412. As shown in FIG. 24, distal end 418, of the scoring structure may be coupled to the distal tip 414 of the catheter body by an end cap 416. The end cap 416 may be composed of a compatible polymer and thermally bonded with the catheter body to fix distal end 418 of the scoring structure to the catheter body.

Figure 25:
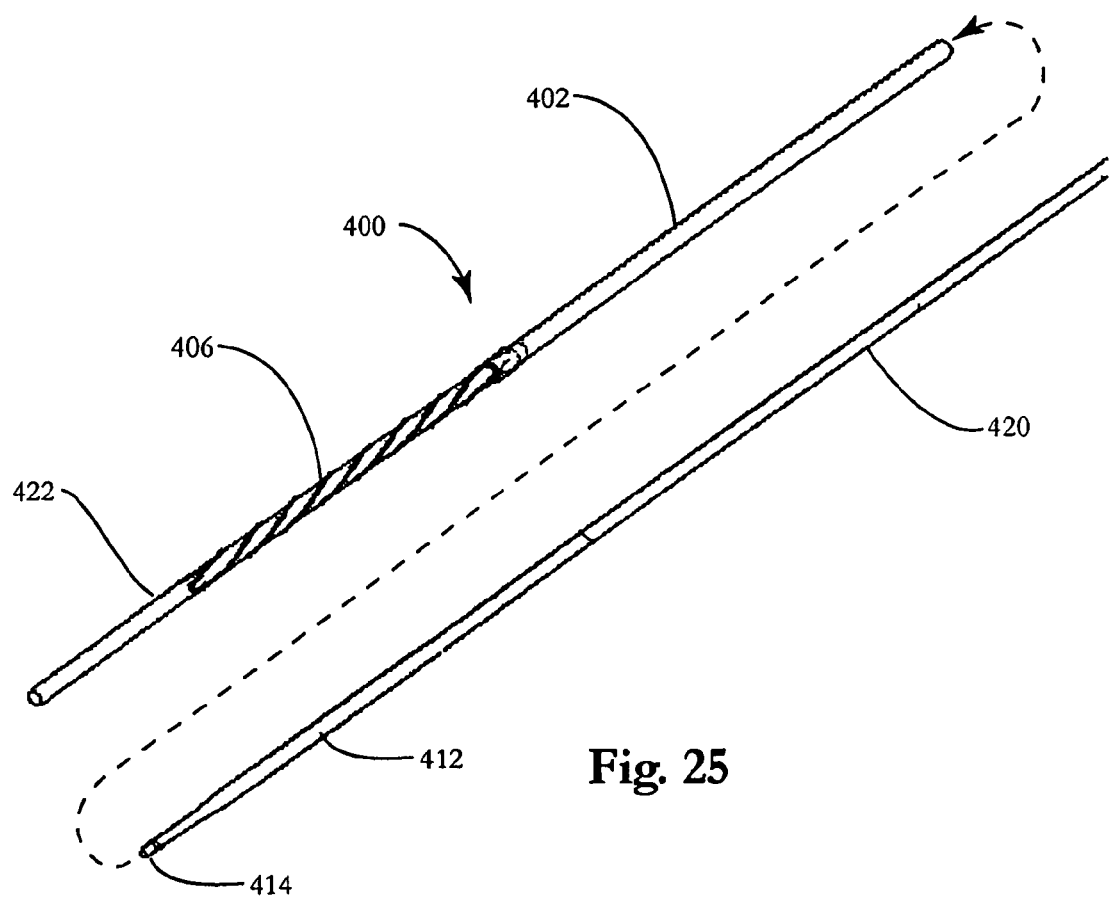
FIG. 25 illustrates a method of the present invention utilizing an insertion tube to mount the scoring structure over the expandable balloon.
Figure 26:
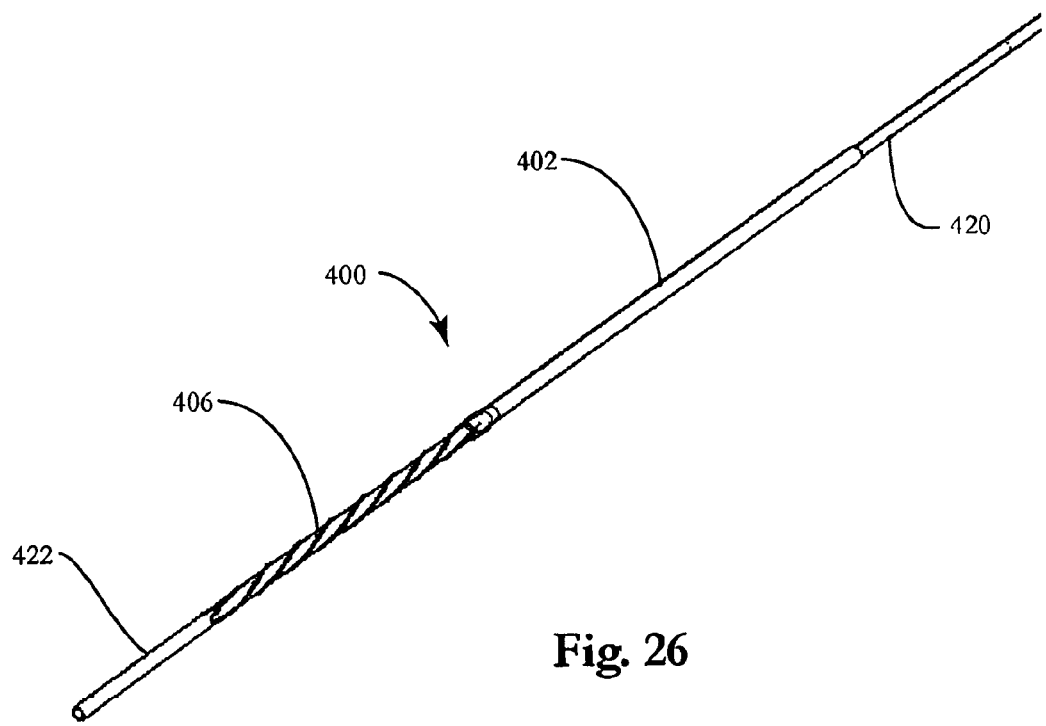
FIG. 26 illustrates shows the insertion tube inserted over the expandable balloon.
Figure 27:
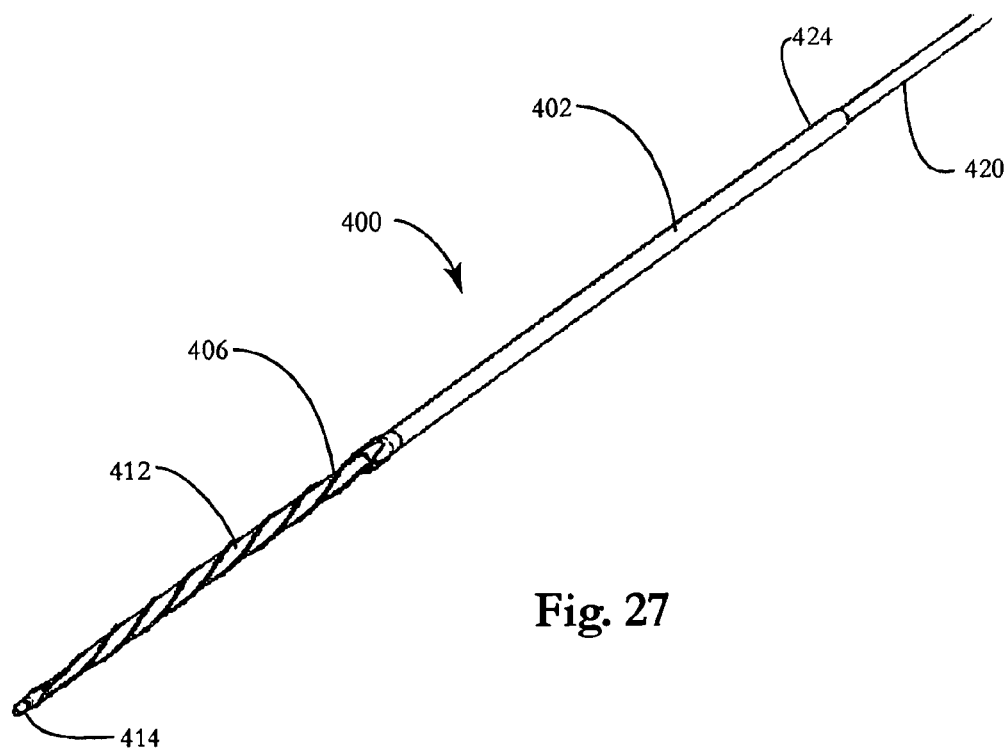
FIG. 27 illustrates a scoring catheter of the present invention with the insertion tube removed.

Now referring to FIGS. 25-27, a method is illustrated for mounting an expandable scoring cage 406 over a balloon catheter. The scoring cage 406 is pre-expanded by loading it over an insertion tube 422 that has an inner diameter slightly larger than the outer diameter of the balloon 412. A catheter body 420 having a balloon 412 is then inserted into the inner diameter of the insertion tube 422 and advanced until the balloon 412 is appropriately positioned with respect to the scoring structure 406, as illustrated in FIG. 26. The insertion tube 422 is then pulled back to allow the expanded scoring structure to collapse over the balloon 412 and the catheter body 420, as shown in FIG. 27. The scoring structure 406 may then be secured at its distal end 418 to the distal tip 414 of the catheter body 420 and the proximal end 424 of the scoring structure/attachment structure assembly to a medial location on the catheter body 420.

It will be appreciated by persons skilled in the art that the present invention is not limited to what has been particularly shown and described hereinabove. Alternate embodiments are contemplated that fall within the scope of the invention.

What is claimed is:

1. An angioplasty catheter comprising:
    a catheter body having a proximal end and a distal end;
    a radially expandable shell near the distal end of the catheter body;
    an external structure carried over but unattached to the shell, wherein the external structure has a distal end fixedly attached to the catheter body at a location distal to the radially expansible shell so that a proximal end of the external structure is drawn distally axially and/or rotates relative to the catheter body as the shell is radially expanded; and
    an attachment structure having a proximal end fixedly attached to the catheter body and a distal end attached to the proximal end of the external structure, wherein the attachment structure is sufficiently sized and compliant to accommodate movements of the external structure relative to the catheter body which are produced by the external structure as it is expanded by the shell wherein the attachment structure comprises an elastic polymeric compliance tube having an outer diameter and an inner diameter that extends over the catheter body, wherein the distal end of the compliance tube does not extend over the radially expansible shell.

2. A catheter as in claim 1, wherein the external structure comprises a scoring structure.

3. A catheter as in claim 1, wherein the external structure comprises a cutting structure.

4. A catheter as in claim 1, wherein at least a portion of the external structure is arranged helically over the shell.

5. A catheter as in claim 1, wherein the attachment structure twists to accommodate rotation of the external structure as the shell is expanded.

6. A catheter as in claim 1, wherein the inner diameter of the compliance tube is larger than an outer diameter of the catheter body so that the compliance tube can narrow as it lengthens with respect to the catheter body as the external structure foreshortens.

7. A catheter as in claim 1, wherein the compliance tube is composed of a polymer is selected from the group consisting of nylon and Pebax.

8. A catheter as in claim 7, wherein the compliance tube has a wall thickness ranging from 0.001 in. to 0.1 in.

9. A catheter as in claim 8, wherein the compliance tube has a length ranging from 1 cm to 10 cm.

10. A catheter as in claim 1, wherein a distal end of the compliance tube is laminated over a proximal end of the external structure.

11. A catheter as in claim 10, wherein a sleeve is laminated to the compliance tube using a thermal bond.

12. A catheter as in claim 10, wherein a sleeve is laminated to the compliance tube with an adhesive.

13. A catheter as in claim 10, wherein the end of the external structure is fixed to a distal end of the catheter body.

14. A catheter as in claim 1, wherein the compliance tube has one or more perforations.

15. A catheter as in claim 14, wherein the one or more perforations comprise one or more slots extending along the outside circumference of the compliance tube.

16. A catheter as in claim 15, wherein the slots form a pattern along the outside circumference of the compliance tube.

17. A catheter as in claim 16, wherein the slots are parallel to each other.

18. A catheter as in claim 16, wherein the slots extend helically across the compliance tube.

19. A catheter as in claim 16, wherein the slots extend radially across the compliance tube.

20. A catheter as in claim 16, wherein the slots are circular in shape.

21. A catheter as in claim 16, wherein the slots are rectangular in shape.

22. A catheter as in claim 1, wherein the compliance tube has an outer diameter that tapers from its distal end to its proximal end.

23. A catheter as in claim 22, wherein the outer diameter of the compliance tube tapers down from in the range of 0.004 in. to 0.010 in. from the distal end and to the proximal end.

24. A catheter as in claim 1, wherein the attachment structure is connected at its proximal end to a manipulator.

25. A catheter as in claim 24, wherein the manipulator is positioned at the proximal end of the catheter body and the attachment structure extends from the external structure across the length of the catheter body.

26. A catheter as in claim 24, wherein the attachment structure axially extends to accommodate foreshortening of the external structure as the shell is expanded.

27. A catheter as in claim 26, wherein the attachment structure twists to accommodate rotation of the external structure as the shell is expanded.

28. A catheter as in claim 27, wherein the attachment structure comprises a compliance tube having an outer diameter and an inner diameter that extends over the catheter body.

29. A catheter as in claim 28, wherein the inner diameter of the compliance tube is larger than an outer diameter of the catheter body so that the compliance can lengthen and twist with respect to the catheter body as the external structure foreshortens.

30. A catheter as in claim 29, wherein the compliance of the external structure is controlled by actuating the manipulator during expansion of the radially expansible shell.

31. A catheter as in any of claim 30, wherein actuating the manipulator comprises axially advancing the attachment structure with respect to the catheter body.

32. A catheter as in claim 31, wherein axially advancing the attachment structure comprises pulling the attachment structure away from the distal end of the catheter body.

33. A catheter as in any of claim 30, wherein actuating the manipulator comprises rotating the attachment structure with respect to the catheter body.

34. A catheter as in claim 29, wherein the compliance of the external structure is controlled by actuating the manipulator during contraction of the radially expandable shell.

35. A method of dilating a stenosed region in a blood vessel, the method comprising:
   introducing an external structure having a distal end and a proximal end carried over an expandable shell, wherein the external structure is unattached to the shell, the distal end is fixedly attached to a catheter body, and the proximal end is connected to the catheter body by an attachment structure; and
   expanding the expandable shell to dilate external structure within the stenosed region within the blood vessel, wherein the proximal end of the external structure moves distally and the attachment structure axially lengthens to accommodate such distal movement of the external structure as the shell is expanded, wherein the attachment structure comprises a compliance tube having an outer diameter and an inner diameter, wherein the compliance tube extends over the catheter body.

36. A method as in claim 35, wherein the attachment structure further accommodates rotation of the external structure as the shell is expanded.

37. A method as in claim 36, wherein the external structure has a proximal end and a distal end, and wherein the proximal end of the attachment structure is fixed to the catheter body.

38. A method as in claim 36, wherein the external structure has a proximal end and a distal end, and wherein the method further comprises the step of fixing the proximal end of the attachment structure to a manipulator.

39. A method as in claim 38, wherein the manipulator is positioned at the proximal end of the catheter body and the attachment structure extends from the external structure across the length of the catheter body.

40. A method as in claim 39, wherein the compliance of the external structure is controlled by actuating the manipulator during expansion of the radially expandable shell.

41. A method as in any of claim 40, wherein actuating the manipulator comprises axially advancing attachment structure with respect to the catheter body.

42. A method as in claim 41, wherein axially advancing attachment structure comprises pulling the attachment structure away from the distal end of the catheter body.

43. A method as in any of claim 40, wherein actuating the manipulator comprises rotating the attachment structure with respect to the catheter body.

44. A method as in claim 39, wherein the compliance of the external structure is controlled by actuating the manipulator during contraction of the radially expandable shell.

45. A method as in claim 35, wherein the inner diameter of the compliance tube is larger than an outer diameter of the catheter body so that the compliance tube freely lengthens and rotates with respect to the catheter body as the external structure foreshortens.

46. A method as in claim 45, wherein the compliance tube has a wall thickness ranging from 0.001 in. to 0.1 in.

47. A method as in claim 46, wherein the compliance tube has a length ranging from 1 cm to 10 cm.

48. A method as in claim 35, wherein the compliance tube comprises an elastic material.

49. A method as in claim 48, wherein the compliance tube comprises a polymer.

* * * * *